US007445891B2

(12) United States Patent
Taylor

(10) Patent No.: US 7,445,891 B2
(45) Date of Patent: Nov. 4, 2008

(54) NUCLEIC ACID TRIGGERED CATALYTIC DRUG AND PROBE RELEASE

(76) Inventor: John-Stephen Taylor, 456 Staines Ct., St. Louis, MO (US) 63141

(*) Notice: Subject to any disclaimer, the term of this patent is extended or adjusted under 35 U.S.C. 154(b) by 0 days.

(21) Appl. No.: 10/201,680

(22) Filed: Jul. 23, 2002

(65) Prior Publication Data
US 2003/0060441 A1 Mar. 27, 2003

Related U.S. Application Data

(60) Provisional application No. 60/307,275, filed on Jul. 23, 2001.

(51) Int. Cl.
*C12Q 1/68* (2006.01)
*C12N 9/16* (2006.01)
*C12N 15/63* (2006.01)
*C12P 19/34* (2006.01)
*C07H 21/04* (2006.01)

(52) U.S. Cl. .................. 435/6; 435/91.1; 435/91.31; 435/196; 435/455; 536/23.1; 536/24.31; 536/24.5

(58) Field of Classification Search .................. 514/44, 514/1, 2; 435/6, 91.1, 91.31, 455, 458, 196; 536/23.1, 24.5, 24.31
See application file for complete search history.

(56) References Cited

U.S. PATENT DOCUMENTS

| 4,670,379 A * | 6/1987 | Miller .................... 435/6 |
| 4,822,733 A * | 4/1989 | Morrison ................. 435/6 |
| 4,980,482 A | 12/1990 | Frazier |
| 6,384,022 B1 * | 5/2002 | Jackson et al. ............. 514/121 |
| 6,657,052 B1 * | 12/2003 | Turnbull ................... 536/23.1 |

FOREIGN PATENT DOCUMENTS

WO    WO 0024426 A1 *  5/2000

OTHER PUBLICATIONS

Webster's II New Riverside University Dictionary 1994 Houghton Mifflin Company. pp. 284 and 484.*
Ma et al. Nucleic acid-triggered catalytic drug release Oct. 2000 Proc. Natl. Acad. Sciences. vol. 97(21):pp. 11159-11163.*
Ma et al., Proc. Natl. Acad. Sci., vol. 97, No. 21, pp. 11,159-11,163 (2000).*
Moss et al., International J. of Pharmaceutics, vol. 74, pp. 67-75 (1991).*
Moss et al., International J. of Pharmaceutics, vol. 66, pp. 39-45 (1990).*
Fox, S.W. and Minard, F.N., Studies on Antipodes. VIII. Synthesis of a Series of Valine Derivatives. *J. Am. Chem. Soc.*, (1952), 74, 2085-2087.
Bender, M.L. and Turnquest, B.W., The imidazole-catalyzed hydrolysis of p-nitrophenyl acetate. *J. Am. Chem. Soc.*, (1957), 79, 1652-1655.

Bruice, T.C. and Schmir, G.L., Imidazole catalysis. I. The catalysis of the hydrolysis of phenyl acetates by imidazole. *J. Am. Chem. Soc.*, (1957), 79, 1663-1667.
Bruice, T.C. and Sturtevant, J.M., Imidazole catalysis. V. The intramolecular participation of the imidazolyl group in the hydrolysis of some esters and the amide of gamma-(4-imidazolyl)-butyric acid and 4-(2'-acetoxyethyl)-imidazole. *J. Am. Chem. Soc.*, (1959), 81, 2860-2870.
Milstien, J.B. and Fife, T.H., Steric effects in the imidazole-catalyzed hydrolysis of esters of N-acetylserinamide and of p-nitrophenol. *J. Amer. Chem. Soc.*, (1968), 90, 2164-8.
Walder, J.A., Walder, R.Y., Heller, M.J., Freier, S.M., Letsinger, R.L. and Klotz, I.M., Complementary carrier peptide synthesis: general strategy and implications for prebiotic origin of peptide synthesis. *Proc Natl Acad Sci U S A*, (1979), 76, 51-55.
Lewis, R.J. and Hanawalt, P.C., Ligation of oligonucleotides by pyrimidine dimers-a missing 'link' in the origin of life? *Nature*, 298, (1982), 393-396.
Chakravarty, P.K., Carl, P.L., Weber, M.J. and Katzenellenbogen, J.A., Plasmin-activated prodrugs for cancer chemotherapy. 1. Synthesis and biological activity of peptidylacivicin and peptidylphenylenediamine mustard. *J. Med. Chem.*, (1983), 26, 633-638.
Cardullo, R.A., Agrawal, S., Flores, C., Zamecnik, P.C. and Wolf, D.E., Detection of nucleic acid hybridization by nonradiative fluorescence resonance energy transfer. *Proc Natl Acad Sci USA*, (1988), 85, 8790-8794.
Rao, K.R., Srinivasan, T.N., Bhanumathi, N. and Sattur, P.B., Artificial enzymes: synthesis of imidazole substituted at C(-2) of β-cyclodextrin as an efficient enzyme model of chymotrypsin. *J. Chem. Soc., Chem. Commun.*, (1990), 10-11.
Andrianomenjanahary, S., Dong, X.., Florent, J.C., Gaudel, G., Gesson, J.P., Jacquesy, J.C., Koch, M., Michel, S., Mondon, M., Monneret, C., Petit, P., Renoux, B. and Tilliquin, F., Synthesis of novel targeted pro-prodrugs of anthracyclines potentially activated by a monoclonal antibody galactosidase conjugate. (Part 1). *Bioorganic & Medicinal Chemistry Letters*, (1992), 2, 1093-1096.
Gryaznov, S.M. and Letsinger, R.L., Chemical Ligation of Oligonucleotides in the presence and Absence of a Template. *J. Am. Chem. Soc.*, (1993), 115, 3808-3809.
Gryaznov, S.M. and Letsinger, R.L., Template controlled coupling and recombination of oligonucleotide blocks containing thiophosphoryl groups. *Nucleic Acids Res.*, (1993), 21, 1403-1408.
Arar, K., Monsigny, M. and Mayer, R., Synthesis of oligonucleotide-peptide conjugates containing a KDEL signal sequence. *Tetrahedron Lett.*, (1993), 34, 8087-8090.
Mergny, J.L., Boutorine, A.S., Garestier, T., Belloc, F., Rougee, M., Bulychev, N.V., Koshkin, A.A., Bourson, J., Lebedev, A.V., Valeur, B., Thuong, N.T. and Helene, C., Fluorescence energy transfer as a probe for nucleic acid structures and sequences. *Nucleic Acids Res*, (1994), 22, 920-8.

(Continued)

*Primary Examiner*—Jane Zara
(74) *Attorney, Agent, or Firm*—Sonnenschein, Nath & Rosenthal LLP

(57) ABSTRACT

The present invention provides methods and combinations of compositions for the modulation of diseases caused by a subject possessing a disease-specific nucleic acid sequence. Included are methods for the treatment, prevention and/or inhibition of the diseases by administering a combination of a prodrug component, drug and catalytic component such that the drug is catalytically released when contacting the combination to the disease-specific nucleic acid sequence.

31 Claims, 19 Drawing Sheets

OTHER PUBLICATIONS

Herrlein, M.K. and Letsinger, R.L., Selective chemical autoligation on a double-stranded DNA template. *Nucleic Acids Res*, (1994), 22, 5076-5078.

Gryaznov, S.M., Schultz, R., Chaturvedl, S.K. and Letsinger, R.L., Enhancement of selectivity in recognition of nucleic acids via chemical autoligation. *Nucleic Acids Res.*, (1994), 22, 2366-2369.

Hovinen, J., Guzaev, A., Azhayeva, E., Azhayev, A. and Lönberg, H., Imidazole Tethered Oligodeoxyribonucleotides: Synthesis and RNA Cleaving Activity. *J. Org. Chem.*, (1995), 60, 2205-2209.

Dobrikov, M.I., Gaidamakov, S.A., Gainutdinov, T.I., Koshkin, A.A. and Vlassov, V.V., Sensitized photomodification of single-stranded DNA by a binary system of oligonucleotide conjugates. *Antisense Nucleic Acid Drug Dev*, (1997), 7, 309-317.

Xu, Y.Z. and Kool, E.T., A novel 5'-iodonucleoside allows efficient nonenzymatic ligation of single stranded duplex DNAs. *Tetrahedron Lett.*, (1997), 38, 5595-5598.

Schmidt, F., Florent, J.C., Monneret, C., Straub, R., Czech, J., Gerken, M. and Bosslet, K., Glucuronide prodrugs of hydroxy compounds for antibody directed enzyme prodrug therapy (ADEPT): a phenol nitrogen mustard carbamate. *Bioorg. Med. Chem. Lett.*, (1997), 7, 1071-1076.

Liu, J. and Taylor, J.S., Template-directed photoligation of oligodeoxyribonucleotides via 4-thiothymidine. *Nucleic Acids Res*, (1998), 26, 3300-3304.

Koppitz, M., Nielsen, P.E. and Orgel, L.E., Formation of oligonucleotide-PNA-chimeras by template-directed ligation. *J Am Chem Soc*, (1998), 120, 4563-4569.

Denny, W.A. and Wilson, W.R., The design of selectively-activated anti-cancer prodrugs for use in antibody-directed and gene-directed enzyme-prodrug therapies. *J Pharm Pharmacol*, (1998), 50, 387-394.

Sakthivel, K. and Barbas, C.F., III, Expanding the potential of DNA for binding and catalysis: highly functionalized dUTP derivatives that are substrates for thermostable DNA polymerases. *Angew. Chem., Int. Ed.*, (1998), 37, 2872-2875.

Melton, R., Connors, T. and Knox, R.J., The use of prodrugs in targeted anticancer therapies. *S.T.P. Pharma Sci.*, (1999), 9, 13-33.

Dubowchik, G.M. and Walker, M.A., Receptor-mediated and enzyme-dependent targeting of cytotoxic anticancer drugs. *Pharmacol Ther*, (1999), 83, 67-123.

Thurston, D.E., Nucleic acid targeting: therapeutic strategies for the 21st century. *Br. J. Cancer*, (1999), 80, 65-85.

Dobrikov, M.I., Gainutdinov, T.I. and Vlassov, V.V., Visible light activatable binary system of oligonucleotide conjugates for nucleic acids modification. *Nucleosides & Nucleotides*, (1999), 18, 1517-1518.

Madec-Lougerstay, R., Florent, J.-C. and Monneret, C., Synthesis of self-immolative glucuronide spacers based on aminomethylcarbamate. Application to 5-fluorouracil prodrugs for antibody-directed enzyme prodrug therapy. *J. Chem. Soc., Perkin Trans*, (1999) 1, 1369-1376.

Sei-Iida, Y., Koshimoto, H., Kondo, S. and Tsuji, A., Real-time monitoring of in vitro.transcriptional RNA synthesis using fluorescence resonance energy transfer. *Nucleic Acids Res*, (2000), 28, E59 (7 pages).

Tsuji, A., Koshimoto, H., Sato, Y., Hirano, M., Sei-Iida, Y., Kondo, S. and Ishibashi, K., Direct observation of specific messenger RNA in a single living cell under a fluorescence microscope. *Biophys J*, (2000), 78, 3260-3274.

Ray, A. and Norden, B., Peptide nucleic acid (PNA): its medical and biotechnical applications and promise for the future. *Faseb J*, (2000), 14, 1041-60.

* cited by examiner

Nitrobenzylphenol-based Prodrug Systems

Trimethylene Lock-Based Prodrug Systems 5S rRNA in vitro Model System for Folded mRNA and the PNA-based drug (hydroxycoumarin) and catalytic components

NUCLEIC ACID TRIGGERED CATALYTIC DRUG AND PROBE RELEASE

CROSS-REFERENCE TO RELATED APPLICATIONS

This application is based on U.S. Provisional Patent Application No. 60/307,275, filed Jul. 23, 2001, incorporated herein by reference in its entirety.

STATEMENT REGARDING FEDERALLY SPONSORED RESEARCH OR DEVELOPMENT

This invention was made in part with Government support under National Institutes of Health Grants CA40463, RR-02004, RR-05018, RR-07115, and P41RR0954. The Government has certain rights in the invention.

SEQUENCE LISTING

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The invention is a new system for the design of highly selective antiviral and anticancer chemotherapeutic agents that make use of a disease-specific nucleic acid sequence to template the association of a prodrug with a catalyst which catalyzes the release of the drug. The effect of thermodynamics, sterics, and electronics on the rate and specificity of drug and probe release in both two- and three-component model systems, and in human serum are also disclosed.

BACKGROUND OF THE INVENTION

Chemotherapeutic approaches to cure infectious diseases and cancer depend on drugs that are selectively toxic to the disease-causing organism or the diseased cell. Viral infections and cancer pose the greatest challenge for chemotherapy because there is little biochemically to distinguish an infected or cancerous cell from a normal cell, and as a result many currently used drugs show little selectivity. There have been a number of approaches to increasing the selectivity of anticancer agents through the use of immunoconjugates, antibody-, gene-, and bacterial-directed enzymatic activation of prodrugs, and by capitalizing on elevated levels of certain enzymes and receptors within cancer cells. Other approaches have sought to exploit what is known about the molecular mechanisms of cancer to identify new biochemical targets for drugs. While all these methods can in principle lead to more selective chemotherapeutic agents, they are by no means easy to implement.

Recent advances in genomic sequencing and DNA chip technology now make it possible to determine the genetic makeup of diseases such as cancer. This, together with the ability to bind specific mRNA or DNA sequences with oligodeoxynucleotides (ODNs) or analogs such as peptide nucleic acids (PNAs) via simple base-pairing rules, or DNA with polyamides via its own set of rules, has opened the door for new approaches to chemotherapy that make direct use of genetic information. Current approaches in this category can be classified as anti-sense or anti-gene, and are based on specifically binding to, and either interfering with, or damaging, the targeted nucleic acid sequence. What makes these approaches so attractive is the ease by which it would seem possible to tailor chemotherapeutic agents for individual patients based on genetic information that could be obtained about their disease states from DNA chips. As promising as both approaches are, it is difficult to predict the therapeutic effect of targeting a viral or cancer-specific nucleic acid sequence, and in many such applications of antisense technology, the therapeutic effect has been found not to involve an antisense mechanism.

The goal of chemotherapy is to design or discover drugs that are selectively toxic to the diseased cell or the disease-causing organism. This is a quite difficult challenge for cancer chemotherapy, however, because there is often little biochemically to distinguish a normal cell from a cancerous cell. Most chemotherapeutic drugs found by traditional screening approaches have been found to interfere with replication and owe their selectivity to the fact that cancer cells divide more rapidly than normal cells. Unfortunately, the chemotherapeutic indices for these drugs are often quite low. More recently, new approaches to chemotherapy have sought to take advantage of what has been learned about the biochemistry of cancer cells to design more effective drugs. Promising as these approaches are, individual drugs would have to be developed for each type of cancer, and would still be susceptible to drug resistance through mutations in the target enzymes or proteins that are acquired by the rapidly dividing cancer cells.

Another approach to obtaining highly selectively chemotherapeutic agents is to further increase the selectivity of known agents by selectively targeting prodrugs, or prodrug metabolizing enzymes to diseased cells. Most notable among such approaches is ADEPT (antibody directed enzyme prodrug therapy), in which an antibody that recognizes a disease-specific antigen is linked to a prodrug metabolizing enzyme which leads to the release of a cytotoxic agent outside the cell. A related approach involves targeting of a gene coding for the prodrug metabolizing enzyme (GDEPT) by either chemical or viral methods to activate the prodrug within the cell. Unfortunately, the success of these types of approaches also depends on the existence of significant biochemical differences between normal and diseased cells, and would likewise be susceptible to drug resistance.

An ideal type of prodrug chemotherapy would involve activation of the prodrug specifically within the diseased cell without the need for targeting, and without the need to know the biochemical basis of the disease.

BRIEF SUMMARY OF THE INVENTION

Among the several aspects of the invention, therefore, is provided a method for the treatment, inhibition or prevention of a disease in a subject caused by the subject possessing a predetermined disease-specific nucleic acid sequence, said method comprising administering to the subject a therapeutically effective amount of a combination comprising a prodrug component, drug and catalytic component wherein the drug is catalytically released upon contacting the prodrug and catalytic components with the disease-specific nucleic acid sequence.

In another aspect, a method is provided for the treatment, inhibition or prevention of a disease in a subject caused by the subject possessing a predetermined disease-specific nucleic acid sequence with a combination comprising a prodrug component, drug and catalytic component wherein the catalytic component is directly fused to the disease-specific nucleic acid sequence by a hairpin loop.

In yet another aspect, a method is provided for killing a diseased cell, said disease caused by a disease-specific nucleotide sequence, comprising hybridizing the disease-specific nucleotide sequence with a prodrug component and a catalytic component capable of converting the prodrug to a drug.

In a further aspect of the invention, combinations are provided comprising a prodrug component, drug and catalytic component wherein the drug is catalytically released upon contacting the prodrug with a disease-specific nucleic acid sequence.

Finally, combinations wherein the catalytic component is directly fused to the disease-specific nucleic acid sequence by a hairpin loop are provided.

Other objects and features of the invention will be in part apparent and in part pointed out hereinafter.

Figure 1:
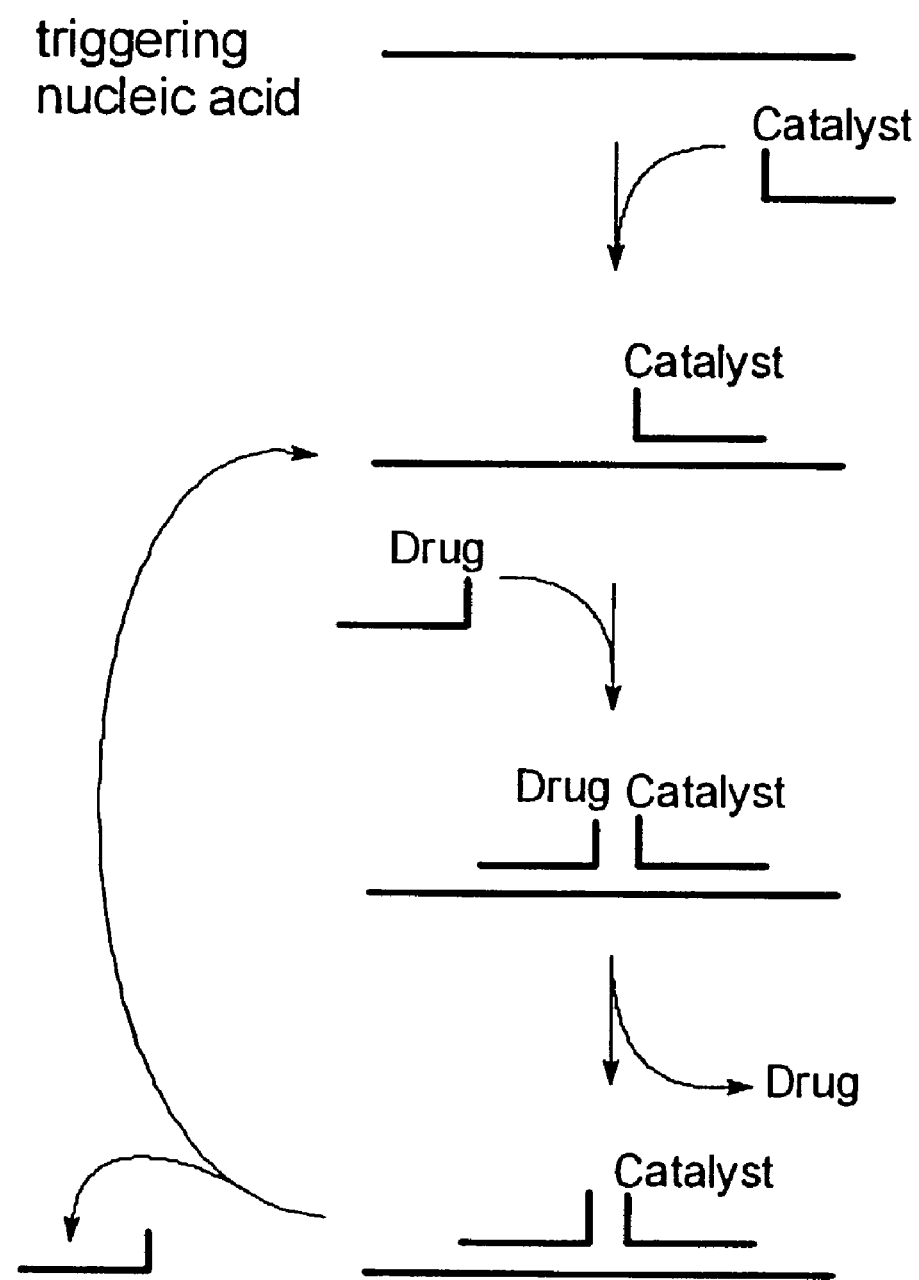
FIG. 1. Schematic of nucleic acid triggered catalytic drug release. The triggering nucleic acid sequence may be either an mRNA or duplex DNA sequence specific to the disease state. The catalyst and drug may be attached to any sequence specific single or double strand binding agent, such as an ODN or analog such as PNA, or a minor groove binding polyamide. Preferably, the drug releasing catalytic component binds tightly to the triggering sequence to form an enzyme-like catalyst, whereas the prodrug binds reversibly, so that it can be exchanged for another prodrug following release of the drug.

More detailed descriptions of the Figures are contained in the relevant portions of the following specification.

DETAILED DESCRIPTION OF THE INVENTION

Disclosed is a new vehicle for the rational design and synthesis of highly selective chemotherapeutic agents that makes direct use of genetic information about the disease state. The invention uses mRNA or DNA specific to a disease state to trigger the catalytic release of a cytotoxic drug, probe or other chemical of interest (hereinafter "drug") by promoting the association of a prodrug or chemical precursor (hereinafter "prodrug") with a catalyst capable of releasing the drug. One embodiment of such an approach in vitro uses a system that is based on the hydrolysis of p-nitrophenylesters by imidazole. More particularly, the catalytic component consists of an imidazole group linked to the 5'-end of a 15-mer that is complementary to the 5'-end of the triggering ODN. The corresponding prodrug component consists of a p-nitrophenol ester linked to the 3'-end of an 8-mer ODN that is complementary to 3'-end of the triggering sequence. This system efficiently releases p-nitrophenol in the presence of all three components, and that the reaction is catalytic and undergoes multiple turnovers. The complex between the catalytic component and the triggering ODN behaves like an enzyme and follows Michaelis-Menten kinetics, with a $K_M$ of 22 mM and a $k_{cat}$ of 0.018 min$^{-1}$. Such catalytic release of p-nitrophenol is sensitive to the presence of a single base pair mismatch.

This new and general vehicle for the rational design of highly selective chemotherapeutic agents that also makes use of the ease by which molecules can be synthesized to recognize specific nucleic acid sequences. Using this approach, referred to as nucleic acid triggered catalytic drug release, a disease-specific nucleic acid sequence is used not as a chemotherapeutic target, but rather as a trigger to cause the catalytic release of a drug. This approach uses the mRNA or DNA sequence specific to a disease as a template to promote the association of a prodrug and a catalytic component capable of converting the prodrug to a drug, which then kills the diseased cell. In this approach, the disease-specific sequence could either be a unique sequence, or an overexpressed sequence. Unlike anti-sense and anti-gene approaches, the therapeutic effectiveness of this approach depends only on the presence of a disease-specific nucleic acid sequence, and not on its biological activity.

In one formulation of this approach (FIG. 1), the prodrug consists of a drug that is attached to a molecule that binds reversibly to a mRNA or DNA sequence that is specific to the disease (the triggering sequence). The corresponding catalytic component consists of a catalyst attached to another molecule that binds tightly to the site on the triggering sequence that is adjacent to the prodrug binding site. In the diseased cell, the catalytic component will bind to the disease-specific mRNA or DNA sequence to form an enzyme-like complex which contains a prodrug binding site in addition to the catalytic site. Once formed, this catalytic complex will carry out multiple turnovers of prodrug to drug which will result in the death of the diseased cell. In a non-diseased cell lacking the triggering sequence, association of the catalyst with the prodrug will not occur efficiently, and the cell will survive. This approach should also be applicable to diseases in which the triggering sequence differs from the normal one by a single nucleotide, as would be the case for many cancers, because binding of molecules such as ODNs are known to be sensitive to centrally located single base-pair mismatches. The feasibility of this approach is shown below with a system that is based on the ability of imidazole to catalyze the hydrolysis of p-nitrophenol esters.

It is with these criteria in mind that applicant has recently developed a new and general concept for the design of easily programmable and highly selective chemotherapeutic drugs that is termed nucleic acid triggered catalytic drug release. The system converts a disease-specific nucleic acid sequence into a prodrug-metabolizing catalyst specifically within a diseased cell by way of the high specificity and simplicity of Watson-Crick base pairing. In one embodiment of this idea (FIG. 1), the prodrug metabolizing catalyst is created by a catalytic component consisting of a catalytic group attached to an oligonucleotide analog which binds tightly and specifically to a unique site on a disease-specific nucleic acid sequence, such as a unique or overexpressed mRNA sequence. The prodrug in turn consists of a cytotoxic drug that is attached via a cleavable linker to an oligonucleotide analog that binds reversibly to the site adjacent to the catalytic component binding site. When the catalytic component binds to the disease-specific nucleic acid sequence a prodrug metabolizing enzyme-like species is created which contains both a prodrug binding site and a catalytic site. This enzyme-like catalyst then catalyzes multiple releases of a cytotoxic drug from the prodrug. In a normal cell, the disease-specific nucleic acid sequence is either absent, or in low copy number, and the drug will be inefficiently released. The beauty of this approach, is that one only needs to be able to identify the unique or over-expressed nucleic acid sequences that are unique to the diseased cell and not their biological function, something which can now be readily determined by DNA chip technology and other methods known in the art. In the event of a mutation in the triggering sequence, it is quite simple to synthesize a new complementary pair of prodrug and catalytic components to be used in the system. In the event of acquired resistance to the effects of the cytotoxic drug used, a different drug could be readily attached to the prodrug component.

This approach to programmable chemotherapeutic agents is illustrated below with an in vitro three component system based on the imidazole catalyzed hydrolysis of p-nitrophenyl esters. In that example, it is shown that p-nitrophenol is released catalytically and with turnover from a prodrug component consisting of a D-valine-p-nitrophenylester linked octamer ODN and a catalytic component consisting of an imidazole linked 15-mer ODN in the presence of a 23-mer triggering ODN. Below are further examples of this three component and two component systems, as well as examples of a hairpin system which further elucidate the effects of thermodynamics, sterics and electronics on the rate and specificity of drug release using applicants system. Also provided are examples illustrating the effect of substituents and stereochemistry on the stability of the aryl ester subunit of the prodrug component in human serum.

RESULTS AND DISCUSSION

Hairpin Model System

Figure 2:
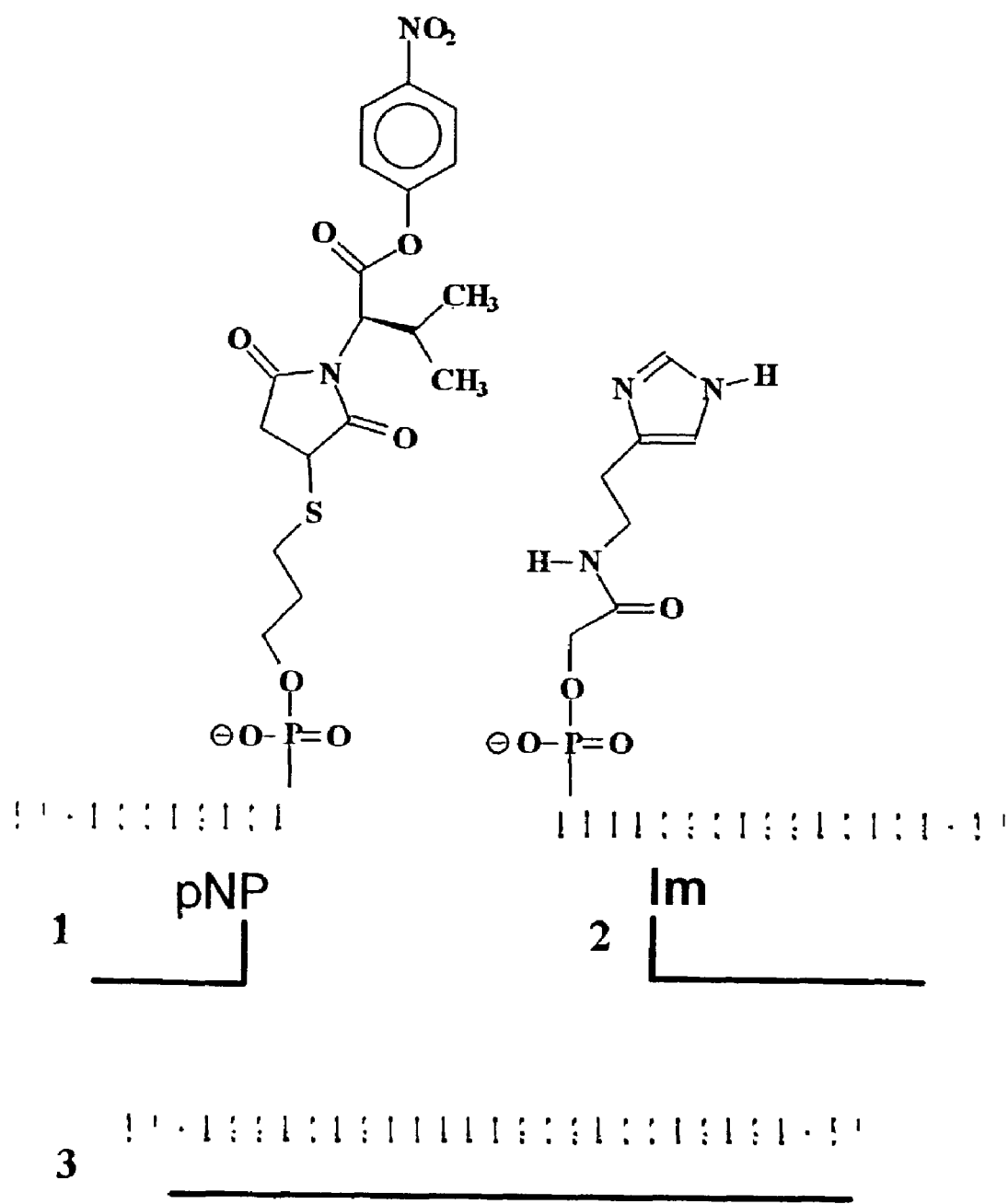
FIG. 2. Three component system of the invention which consists of a prodrug 1 (in this case, SEQ ID NO:1), a catalyst 2 (in this case, SEQ ID NO:2), and a triggering sequence 3 (in this case. SEQ ID NO:3).
Figure 3:
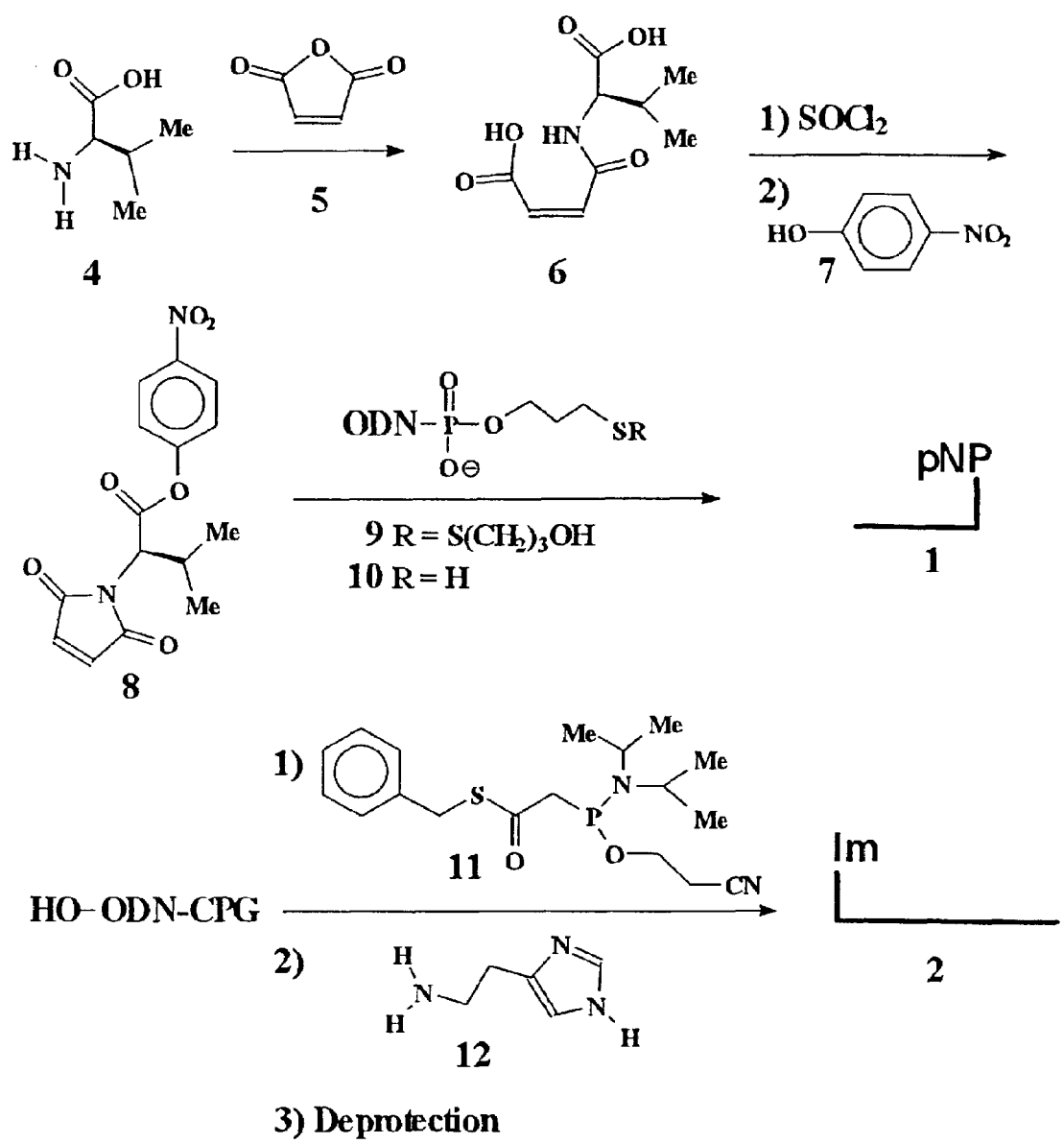
FIG. 3. Synthetic scheme for the preparation of the prodrug and catalyst components.

Applicants have disclosed an embodiment comprising a two component system in which the catalytic component is directly fused to the triggering nucleic acid sequence via a hairpin loop (FIG. 1). This embodiment simplifies the interpretation of the kinetics by reversible binding of the catalytic component to the triggering nucleic acid, and to insure a stoichiometric association between the catalytic component and the triggering component. A d(CTTG) tetraloop flanked by dG and dC was chosen for the hairpin loop since this type of sequence forms a very stable hairpin structure when fused to a five base pair stem. The catalytic group was chosen to be imidazole because it is well known to catalyze the hydrolysis of p-nitrophenylesters as well as other arylesters. In addition, release of a phenol is the key step in the release of cytotoxic drugs such as daunorubicin, phenol mustards, and fluorouracil from hydroxymethylphenyl-based prodrugs, and taxol from trimethylene lock-based prodrugs (FIG. 2). The imidazole is attached to the hairpin by a procedure known to those skilled in the art involving coupling of the thiobenzylester phosphoramidite building block 1 to CPG-supported ODN in the last synthesis cycle to give the intermediate thiobenzylester 2 followed by treatment with excess histamine to give 3a (FIG. 3). Temperature-dependent UV absorbance spectroscopy demonstrates that the hairpin 3a is stable at room temperature, and has a $T_M$ of 65° C. in 0.1 M NaCl, and 75° C. in 1 M NaCl. This compares favorably with the calculated values of 60 and 71° C. respectively and a $T_M$ of 71° C. at 1 M NaCl reported for d(GGAG<u>CTTG</u>CTCC) (SEQ ID NO:18).

Fluorescein Diester Hairpin System

Because of the strong fluorescence and widespread use of fluorescein as a fluorescent probe, the rate of fluorescein release by imidazole catalyzed hydrolysis of diacetyl fluorescein was investigated. Diacetylated fluoresceins are non-fluorescent, but upon hydrolysis of the acyl groups become highly fluorescent. Attempts to attach the N-hydroxysuccinimide derivative of diacetylcarboxyfluorescein via amide bond formation with the 3'-amino linked oligodeoxynucleotide 5 (FIG. 4) failed due to the high pH required for the reaction which led to the premature hydrolysis of the acetate groups. Attempts to conjugate 5-chloromethyl fluorescein diacetate with a 3'-phosphorothioate labeled ODN also failed at pH 7. Coupling could be achieved, however, with the more base-stable pivaloyl derivative 6 by a procedure known to those skilled in the art that has previously been used to link it to 5'-amino linked oligodeoxynucleotide analogs. Three ODNs (7a-c) corresponding to a 4-mer, 6-mer and 8-mer (SEQ ID NOS:7, 8 and 9) were derivatized with bis-pivaloyl fluorescein to test the effect of ODN length on the efficiency of hydrolysis by the imidazole hairpin 3a(SEQ ID NO:4). The TMs of 7a-c were estimated from thermodynamic parameters to be -20, 19, and 41° C. under the conditions of the experiment and have equilibrium dissociation constants of 3.4 mM, 8.1 mM, and 14 nM.

Figure 5:
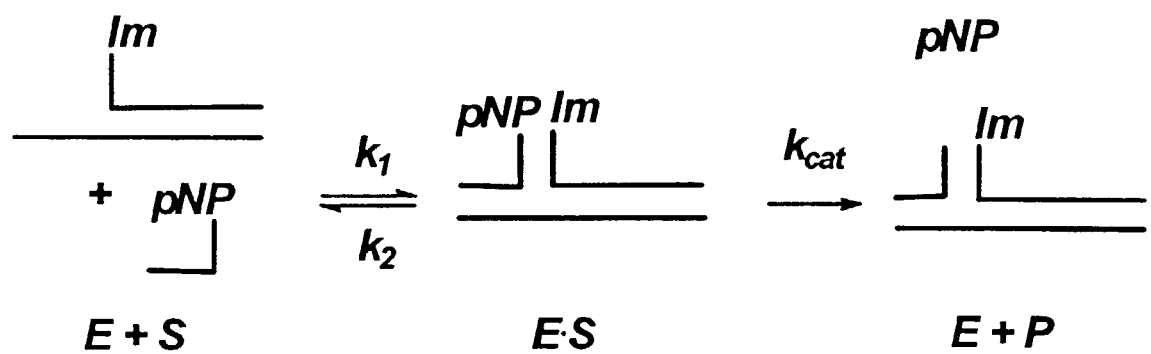
FIG. 5. The complex formed between the catalytic component and the triggering sequence behaves like an enzyme. The kinetics of p-nitrophenol release from the three component system was analyzed according to a Michaelis-Menten mechanism. Shown are Eadie-Hofstee plots of the initial rate data in the presence and absence of a competitor ODN. The initial rates were obtained by analysis of the time dependence of p-nitrophenol release as a function of pNP-8-mer concentration in the presence of 5 mM Im-15-mer and 5 mM 8-mer lacking the p-nitrophenyl ester attachment that were carried out under the conditions described in the FIG. 4 caption. The extrapolated lines were derived from KM and Vmax data obtained from non-linear least squares fit of the kinetic data.
Figure 5:
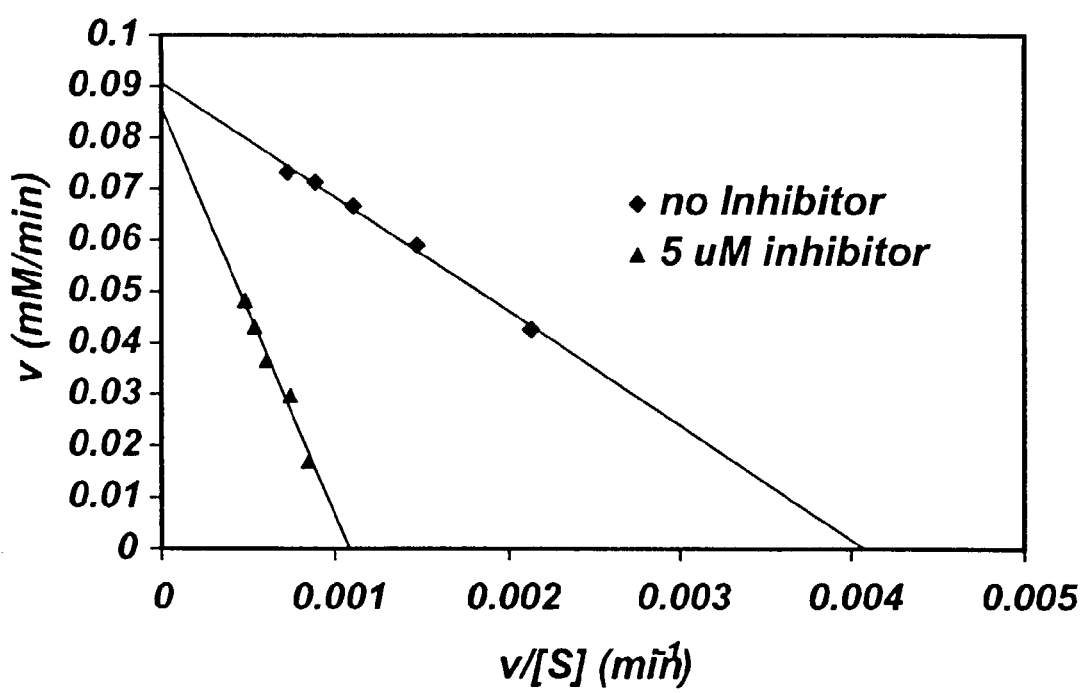

The rate of fluorescein release was greatest for the 8-mer 7c(SEQ ID NO:9) and roughly corresponded to the rate of release observed in 0.01 mM imidazole buffer alone at pH 7 (FIG. 5). The relative initial rates of fluorescein release for 7a-c(SEQ ID NOS:7, 8 and 9) under otherwise identical conditions were 1 : 48 : 493. The observed relative rates are similar to those of 1: 188: 340 that would be predicted based on the initial rate being proportional to $(K_d+[S])^{-1}$ if the system is following a Michaelis-Menten mechanism, given that the concentration of imidazole hairpin enzyme and substrate are the same. In addition, it is assumed that $k_{ca}$ will be the same for all three substrates. Attempts, however, to fit the rate of fluorescein release from 7a-c (SEQ ID NOS:7, 8 and 9) in the presence of 3a(SEQ ID NO:4) to Michaelis-Menten kinetics, or the rate of fluorescein release from fluorescein dipivalate by imidazole to a one or two step mechanism were not successful.

b-Alanine-nitrophenol Hairpin System p-nitrophenolate release was studies because of the greater sensitivity of p-nitrophenyl esters to hydrolysis by base than the pivalate esters. However, it was discovered that the same pH 9 conditions that had worked successfully for coupling of the pivalate esters by amide bond formation could not be used for the b-Alanine-nitrophenol hairpin system. Unfortunately, the yields of amide bond formation at neutral pH by a variety of methods are very poor. One alternative method for coupling peptides to ODNs under neutral conditions involves addition of a thiol derivatized ODN to a maleimide derivatized peptide. A maleimide linked p-nitrophenyl ester 9 (FIG. 6) was prepared by condensing b-alanine with maleic anhydride to form the maleamic acid derivative 8 which was then refluxed with thionyl chloride followed by addition of p-nitrophenol according to a procedure well-known in the art. The resulting maleimide p-nitrophenyl ester 9 was then linked to an ODN 8-mer by reduction of the disulfide protected ODN 14 that was prepared by automated synthesis utilizing a commercially available support.

Figure 7:
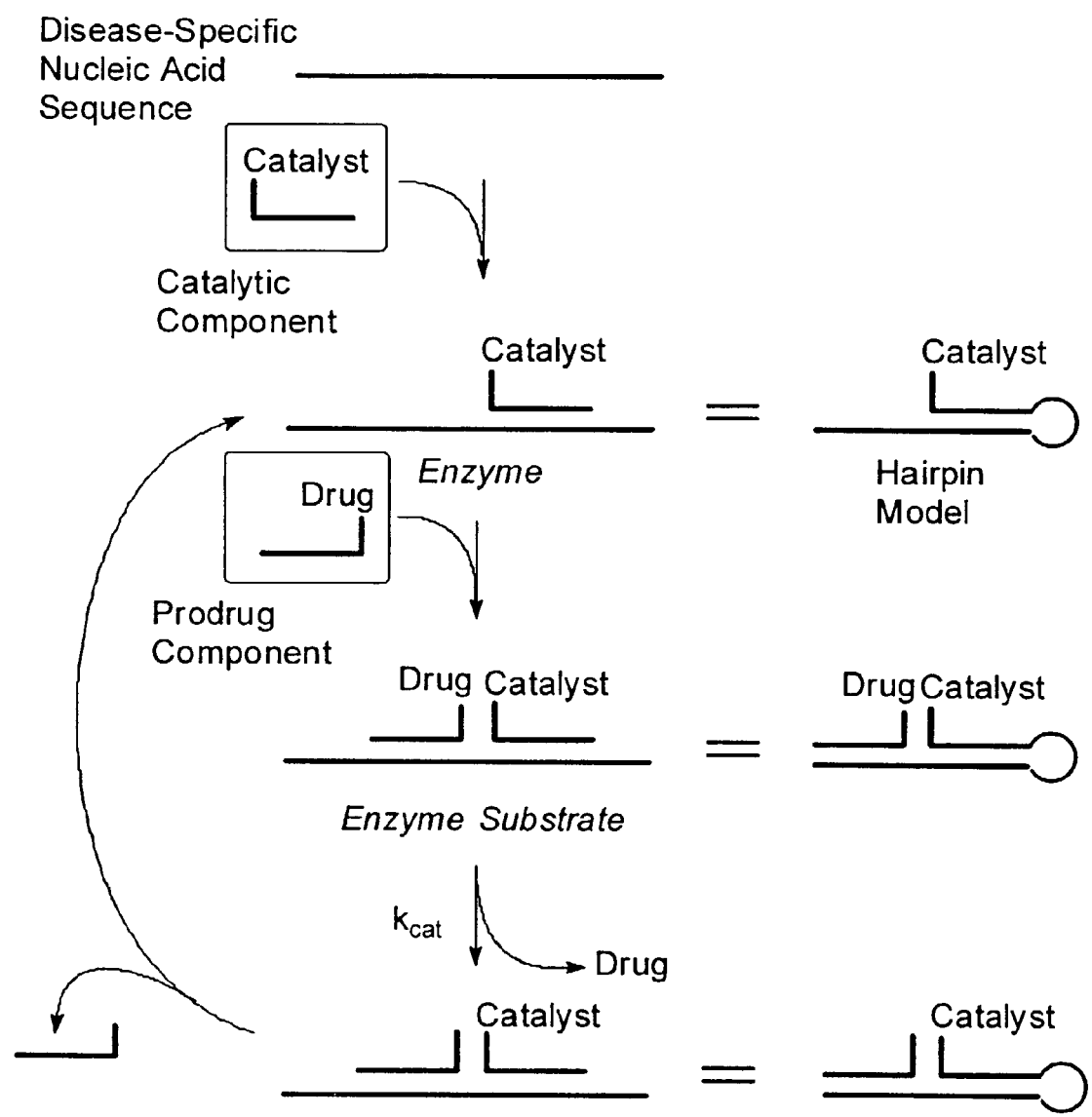
FIG. 7. Nucleic acid triggered catalytic drug release. The system converts a disease specific nucleic acid sequence into a drug releasing enzyme-like catalyst by complex formation with a complementary catalyst-bearing nucleic acid or analog. To the right is a simpler two component model system that can be used to evaluate the catalytic efficiency of various catalyst drug combinations.
Figure 8:
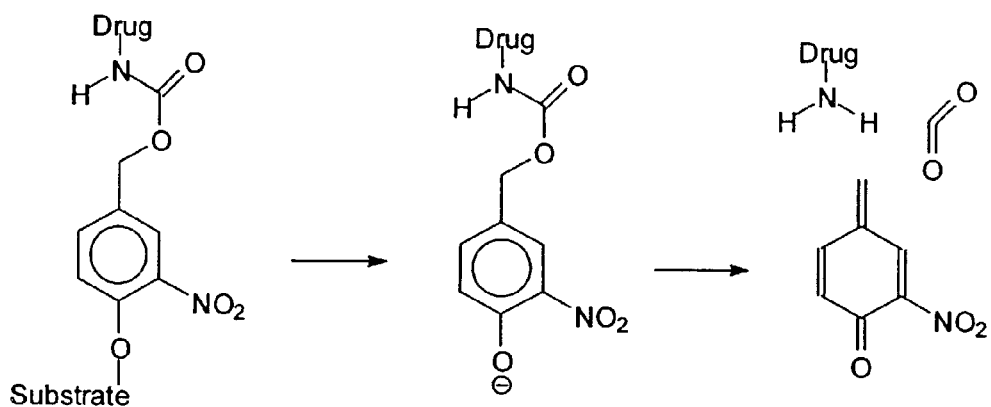
FIG. 8. Prodrugs whose activation is triggered by the initial release of a phenol group.
Figure 8:
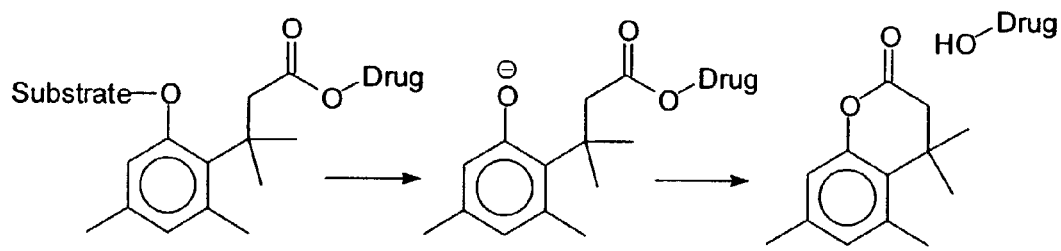

When the prodrug 15a (SEQ ID NO:10) was incubated with the imidazole hairpin 3a (SEQ ID NO:4), catalytic release of p-nitrophenolate was observed that depended on the presence of the imidazole group (FIG. 7). The half life for release of a single p-nitrophenolate is only about 10 mm, and four turnovers are complete in about 4 h. Applicant found that the initial rate of p-nitrophenolate release followed simple Michaelis-Menten kinetics, and was subject to competitive inhibition by the disulfide linked oligodeoxynucleotide 14 (FIG. 8). The experimental $K_i$ and $K_M$ values of 38 and 50 mM (Table 2) are more than three orders of magnitude higher than the expected value of 14 nM for the dissociation constant $K_d$ of the prodrug and inhibitor based on available thermodynamic parameters. One possibility for the large difference between $K_M$ and the calculated $K_d$ values is that $k_{cat}$ is much greater than $k_{off}$. Given that the on rate for duplex formation is weakly temperature and sequence dependent and within an order of magnitude of $10^6 M^{-1} s^{-1}$ for many oligodeoxynucleotides, the sum of $k_{off}$ and $k_{cat}$ would have to be about 50 $s^{-1}$ to account for the observed $K_M$. Given that the experimentally determined $k_{cat}$ value is $2.9 \times 10^{-3} s^{-1}$, $k_{off}$ would have to be 50 $s^{-1}$. Thus, it would appear that $k_{off} >> k_{cat}$ and that p-nitrophenolate release is governed by a Michaelis-Menten mechanism in which $K_M$ essentially equals $K_d$.

The substantially higher $K_I$ and $K_M$ values than predicted is somewhat perplexing, and might be due to destabilizing steric and electrostatic interactions caused by close proximity of the functional groups appended to the 5' and 3'-ends of the ODNs through phosphodiester linkages. It would not appear that much of the destabilization is due to electrostatics, as only a modest increase in $K_M$ from 50 to 80 mM was observed on decreasing the salt concentration from 1 M NaCl to 0.1 M (Table 1). The difference between $K_M$ and the calculated $K_d$ might also be due to the inaccuracy in using thermodynamic parameters obtained close to the $T_M$ to predict equilibrium constants at temperatures much different than the $T_M$ value.

The imidazole hairpin system was found to enhance the rate of ester hydrolysis 446-fold relative to imidazole by comparing the bimolecular rate constant given by $k_{cat}/K_M$ to the bimolecular rate constant for imidazole-catalyzed hydrolysis of p-nitrophenylacetate, $k_{Im}$ (Table 2). Applicant also found that that there was an 11-fold difference in the initial rates of p-nitrophenolate release at 1 M NaCl between the completely complementary substrate-hairpin 3a, (SEQ ID NO:4) 15a (SEQ ID NO:10) (X=G) and a single CC base-pair mismatch resulting from a G↔C transversion in the substrate component 15a (SEQ ID NO:10) (X=C) (FIG. 7). Assuming that the rates are proportional to $(K_d+[S])^{-1}$ for the reasons cited above, the observed 11-fold rate difference would have to be accounted for by a 15-fold increase in the $K_d$ of the mismatch substrate. This is more than three orders of magnitude less than that calculated from standard thermodynamic parameters for the corresponding unmodified ODNs which predict a $5 \times 10^4$ difference in $K_d$ for the corresponding unmodified ODNs. On the other hand, the observed 11-fold rate difference is only about 3-fold less than the 34-fold difference that would be calculated on the basis of the $K_d$ values of 14 nm and 0.6 mM for forming the matched and mismatched duplexes with unmodified ODNs at 20° C.

A similar insensitivity to a mismatch was also observed in our study of a three component system involving a D-valine ester linkage and a TC mismatch in place of TA. In that case only a 1.4-fold difference in rate was observed in 1 M NaCl, which could be increased to a 7.5-fold difference in 0.1 M salt. Based on a $K_M$ of 22 mM at 1 M salt, the 1.4-fold difference in rate the $K_d$ for the mismatched system would have to be only 1.7-fold higher, which is three orders of magnitude less than expected from thermodynamic parameters of unmodified duplexes. These thermodynamic parameters predict $K_d$s for the matched TA and mismatched TC duplexes to be 14 nM and 23 mM at 1 M NaCl, and 0.3 mM and 0.5 mM in 0.1 M NaCl at 20° C. On the other hand, these $K_d$s predict an increase in the relative rates between the matched and mismatched ODNs to increase from 2.2 to 25 on going from 1 M NaCl to 0.1 M NaCl, which compares favorably to the experimentally observed increase of 1.4 to 7.5. Again, these unexpectedly low differences in rates between matched and mismatched substrates might result from unfavorable interactions between the ends of the hairpin and substrate, as well as the inaccuracy of predicting free energy differences at temperatures remote from the $T_M$.

D-valine-p-nitrophenol Hairpin System

To be effective as a prodrug, the chemical linkage between the nucleic acid and the drug must be labile to the catalytic component but at the same time be stable to endogenous enzymes. To increase the stability of the ester linkage between the nucleic acid and the drug activating component, the effect of substituting the b-alanine linkage with the sterically more demanding D-valine linkage was examined. Unnatural D-amino acid esters have been shown to decrease the rate of ester hydrolysis by esterases, proteases and lipases. The D-valine linkage can be introduced by the same methodology used for incorporating the b-alanine ester. When the D-valine ester 16a (SEQ ID NO:10) was used in place of the b-alanine ester 15a (SEQ ID NO:10) with the imidazole hairpin 3a(SEQ ID NO:4), the rate of p-nitrophenolate release dropped significantly. Analysis of the kinetic data by Michaelis-Menten kinetics showed that the loss could be attributed primarily to a 8.3-fold drop in $k_{cat}$ (Table 1). Such a drop in the rate constant is consistent with what has been previously observed to occur to the rate of imidazole catalyzed hydrolysis of p-nitrophenylacetate upon alkyl substitution. When compared to the rate of hydrolysis by imidazole alone (Table 2), the imidazole hairpin was found to accelerate the rate of hydrolysis of the b-alanine and D-valine p-nitrophenylesters to the same extent (446 vs. 429 respectively) as calculated by $(k_{cat}/K_M)k_{Im}$ (Table 1).

D-Valine-7-hydroxycoumarin ester Hairpin System

Figure 6:
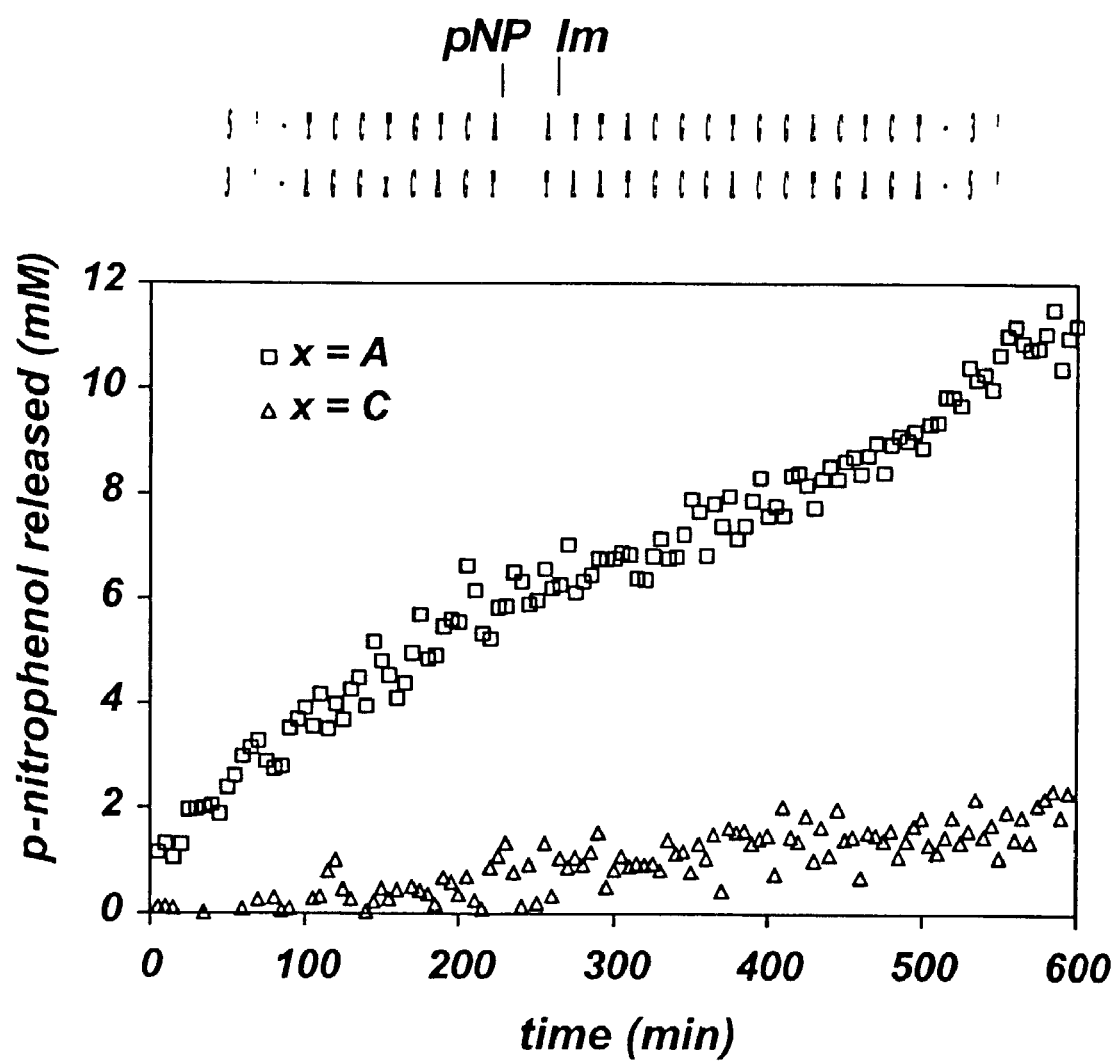
FIG. 6. Catalytic drug release is most efficient for the fully complementary triggering sequence. Im-1-mer (5 mM) (SEQ ID NO:2) was incubated with pNP-8-mer (20 mM) (SEQ ID NO:1) at 20° C. in the presence of the fully matched and singly mismatched 23-mer (5 mM) (SEQ ID NO:3) at pH 7 in a 0.1 M NaCl, 10 mM sodium phosphate buffer.

Whereas the p-nitrophenolate may be a suitable system for drug release, it is not very suitable for diagnostic purposes because of the low sensitivity of absorbance spectroscopy used to detect p-nitrophenolate release. The ability of our imidazole based system to release the well known fluorescent probe 7-hydroxycoumarin otherwise known as umbelliferone was examined. Hydroxycoumarin was linked to the 8-mer through a D-valine linkage to give 16c (SEQ ID NO:10) in the same way used to link the p-nitrophenol (FIG. 6). When incubated with the imidazole hairpin 3a(SEQ ID NO:4), release of the hydroxycoumarin was found to be about 10-fold slower than for p-nitrophenol. Analysis of the kinetics by Michaelis-Menten kinetics established that $k_{cat}$ was about 10-fold lower than for p-nitrophenol release, and that $K_M$ was also lower (Table 1). The 10-fold decrease in $k_{cat}$ was also observed for $k_{Im}$ (Table 2) and is consistent with the higher pKa of 7-hydroxycoumarin than p-nitrophenol (7.8 vs. 7.15) and the known effect of increasing pKa of the phenol group on decreasing the rate of imidazole catalyzed hydrolysis. The lower $K_M$ for hydroxycoumarin release may be due to additional stability imparted by intercalation of the coumarin into the DNA, though this difference in $K_M$ is not apparent for the three component system to be discussed later. When compared to hydrolysis by imidazole alone, a 2,433-fold rate acceleration was calculated (Table 1) which is greater than the rate acceleration of 1,100 observed for hydrolysis of a related hydroxycoumarin by a semisynthetic catalytic antibody.

D-Valine-7-hydroxycoumarin 3-Component System

Having established that the imidazole hairpin could catalyze the release of both p-nitrophenol and hydroxycoumarin that were linked to an 8-mer substrate, the ability of a three component system to release hydroxycoumarin was studied. The kinetics of the three component D-valine-linked p-nitrophenol system in which the imidazole hairpin component is replaced by a imidazole 15-mer 3b (SEQ ID NO:5) which binds to a complementary 23-mer 4 (SEQ ID NO:10) (X=A) that corresponds to a disease-specific triggering sequence are well-known. In this case, the complex formed between the catalytic component 3b (SEQ ID NO:5) and the triggering ODN 4 (X=A) was designed to be highly stable and to function as an enzyme. This is justified considering the predicted kinetics of dissociation of the complex. The 15-mer was calculated to have a $K_d$s at 20° C. of 4.3 fM and 0.012 fM in 0.1 and 1 M NaCl, respectively, and duplex half lives of much greater than a year based on an on rate of $10^6$ $M^{-1}s^{-1}$. As was the case for the three component p-nitrophenol system, release of hydroxycoumarin followed Michaelis-Menten kinetics. As applicant had observed for the imidazole hairpin system, replacing p-nitrophenol with coumarin in the three component system resulted in about a 10-fold decrease in rate that could be attributed to a 10-fold drop in $k_{cat}$ (Table 3). Likewise, the kinetic parameters for both the hairpin and three component systems were also found to be quite similar.

Stability of the Maleimide Esters in Human Serum

Figure 9:
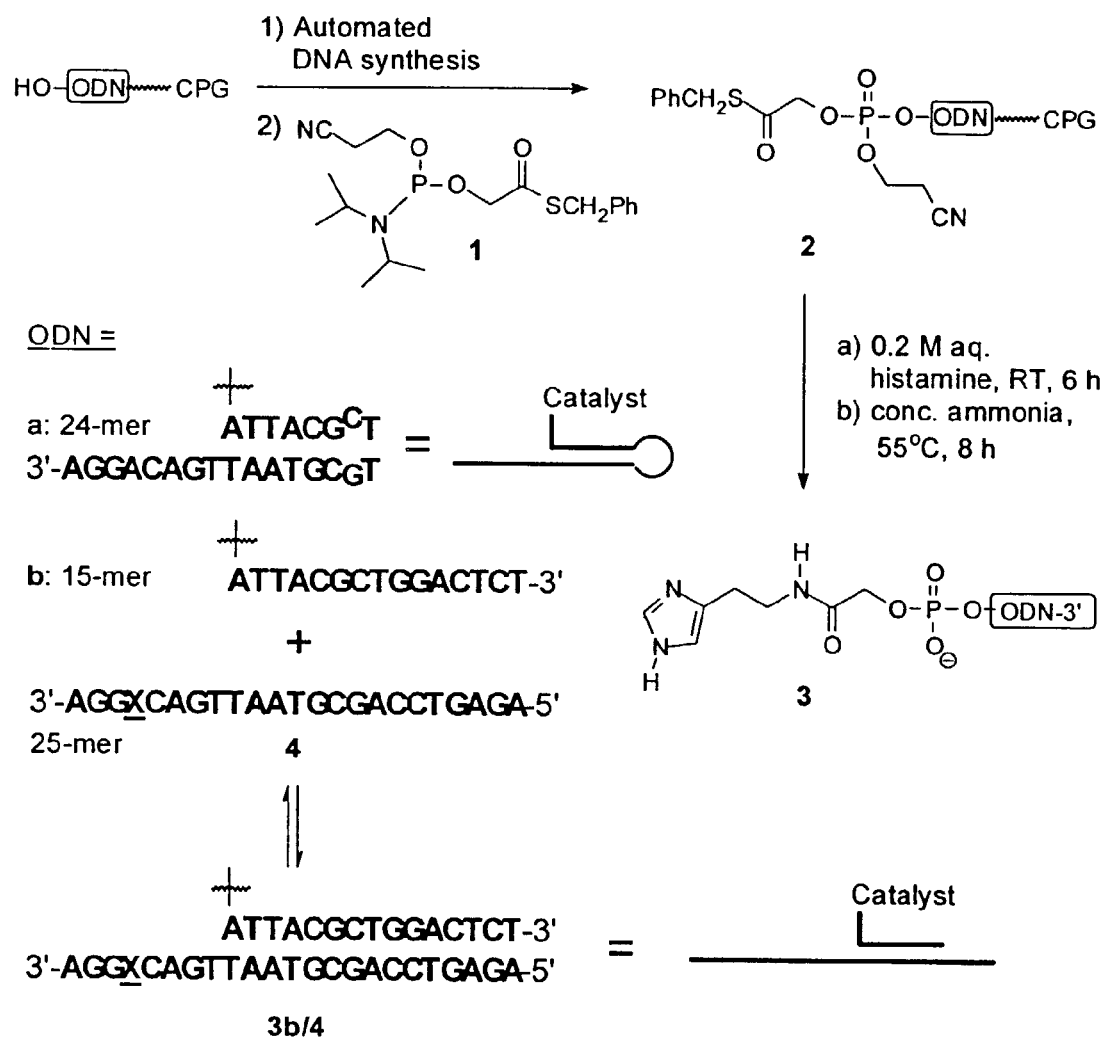
FIG. 9. Synthetic scheme for the preparation of the hairpin enzyme for the two component model system and the catalytic component for the three component system (in this case, the hairpin 24-mer represented by SEQ ID NO:4, the 15-mer represented by SEQ ID NO:5 and the 25-mer represented by SEQ ID NO:6).

To determine whether or not prodrugs or proprobes based on the D-valine ester linkages would be suitable for use in humans applicant investigated the stability of the maleimide esters of o-nitrophenol and 3-hydroxycoumarin D-11b and D-11c in human serum. Applicant found that these two esters are hydrolyzed at a significant rate at 25° C. with a half life of about 3 hours (FIG. 9). Interestingly, the two rates appear to be similar, suggesting that the rate determining step for hydrolysis in serum may not be the initial release of the p-nitrophenol or the hydroxycoumarin, but may instead be the hydrolysis of a rapidly formed acyl enzyme intermediate. Applicant also compared the stability of the D-valine esters to the maleoyl-b-alanine, maleoyl-glycine and CBZ-glycine coumarin esters, 9c, 12c and 13c, and the L-valine ester L-11c. It was found that the maleoyl-b-alanine and maleoyl-glycine esters were more stable than the CBZ-glycine ester, but much less stable than the maleoyl-D-valine esters to hydrolysis by human serum. Presumably, the maleoyl group makes these derivatives poorer substrates for the enzymes involved in the hydrolysis reaction, as there is not a substantial difference in reactivity between these substrates with respect to imidazole catalyzed hydrolysis (Table 2). The stereochemistry at the a-carbon also plays a role, as the D-valine esters are more slowly hydrolyzed by about of factor of about two than the L-valine ester L-11c.

Implications of the Kinetics for Drug or Probe Selectivity in vivo

Two important parameters in determining the maximum degree of selectivity from the nucleic acid triggered drug and probe release system were studied. The first is the number of copies of the triggering nucleic acid in the diseased cell relative to the normal cell, and the second is whether or not the prodrug binding site on the triggering nucleic acid differs in sequence, and hence $K_M$ between the normal and diseased cells. From a simple consideration of the Michaelis-Menten mechanism and the results of this study the relative rates would appear to be given by:

$$\frac{v_{diseased}}{v_{normal}} = \frac{[NA]_{diseased} \cdot (K_d + [prodrug])_{normal}}{[NA]_{normal} \cdot (K_d + [prodrug])_{diseased}}$$

where "[NA]" represents the concentration of the nucleic acid trigger, $K_d$ is the dissociation constant for the drug component binding to the triggering sequence, and "[prodrug]" is the concentration of the prodrug. In deriving this equation, the assumption is made that enough catalytic component is present with high enough binding constant to saturate the nucleic acid trigger and hence the enzyme concentration would equal the concentration of the nucleic acid trigger. The second assumption is that, independent of any specific targeting system, the concentration of drug component would be the same in all cells. A third assumption is that $k_{cat}$ will be the same for any catalytic complex that assembles in either the normal or the diseased cells. Thus, selective drug release could be achieved by either or both the presence of an overexpressed triggering sequence, such as an overexpressed mRNA sequence, or by having the prodrug binding site differ in sequence, and hence different $K_M$. For the latter two cases, it is clear from the derived expression for selectivity, that it would be important to have $K_d$>>prodrug concentration to achieve maximum selectivity.

Another important consideration in designing the nucleic acid catalyzed prodrug releasing components is that they are only activated by the disease-specific nucleic acid sequence, and that drug release is efficient. In humans, a minimum sequence length of 15-17 nucleotides has been suggested to be required to uniquely recognize a specific RNA transcript. In the present invention, the required specificity is embedded within the catalytic component, which by design is composed of a long sequence to anchor it to the mRNA, but which can be more or less than the suggested 15-17 sequence length. Also, as part of the system, the prodrug component must have a sufficient off rate to allow for turnover. If the length of the sequence is too short and hence not specific, the rate of drug release could be inhibited by non-productive binding of the prodrug component to other accessible sites. Thus, preferably, the sequence is of sufficient length to insure specificity of prodrug binding, and of sufficiently low binding affinity to insure that it has a fast enough off rate to allow for rapid turnover. If necessary, low binding affinity may be engineered into the sequence by use of an affinity lowering backbone analog, or appropriate substituents. Accordingly, the number of nucleotides which can be included in the prodrug component can be readily determined by those skilled in the art.

Three Component System

A three component system was designed (FIG. 2) based on the ability of imidazole to catalyze the release of p-nitrophenol from p-nitrophenyl esters. Release of a substituted o- or p-nitrophenol is also the key step in the activation of a recently reported class of prodrugs of the clinically useful chemotherapeutic drug daunorubicin. The model system consists of three components, a prodrug, a catalyst, and a triggering ODN. The catalytic component, Im-15-mer, 2 (SEQ ID NO:2), consists of an imidazole group linked to the 5'-end of a 15-mer that is complementary to the 5'-end of the triggering 23-mer ODN 3 (SEQ ID NO:3). The 15-mer sequence was chosen because it was calculated to have a $T_M$ of 60° C. under the assay conditions, and therefore was expected to form a stable complex with the triggering ODN. The corresponding prodrug component, pNP-8-mer, 1 (SEQ ID NO:1), consists of a p-nitrophenol ester linked to the 3'-end of an 8-mer ODN that is complementary to 3'-end of a 23-mer ODN, 3 (SEQ ID NO:10), representing the triggering sequence. The 8-mer sequence was chosen because it was calculated to have a $T_M$ of 45° C. under the assay conditions, and was expected to form a less stable complex that would bind reversibly to the triggering sequence at 20° C.

The two components were synthesized as shown in FIG. 3. Attachment of the imidazole group was carried out according to a well-known method by coupling a benzyl thioester phosphoramidite 11 to the 5'-end of a CPG-supported d(AT-TACGCTGGACTCT), followed by reaction with histamine 12 to give Im-1-mer 2 (SEQ ID NO:2). In contrast, attachment of a p-nitrophenyl ester to an ODN required a significant amount of experimentation due to the lability of the p-nitrophenylester group at pHs higher than 7 that are typically required for many conjugation reactions. Eventually we found that a p-nitrophenylester could be linked to an ODN at pH 7 by conjugation of the N-maleoyl derivative 8 to 3'-thiolated d(TCCTGTCA) 10 to give pNP-8-mer 1 (SEQ ID NO:1). Other N-maleoyl derivatives of D-valine p-nitrophenyl ester were additionally created because the D-form of amino acid esters with branched side chains are generally poor substrates for esterases, lipases and peptidases. The required N-maleoyl-D-valine ester 8 was prepared by a two step reaction from maleic anhydride 5 and D-valine 4 that proceeds via the maleamic acid intermediate 6 which is cyclized and then esterified with p-nitrophenol 7 in one pot following treatment with thionyl chloride.

Those skilled in the art will recognize that the catalytic component can comprise other catalytic moieties which are capable of catalyzing the release of drugs from prodrug esters. In addition, the catalytic and prodrug components may contain nucleotide sequences of varying length depending on the specificities required or $T_M$s predicted to associate with the disease-specific nucleotide sequence. Those skilled in the art will also recognize that the catalytic and prodrug components may consist of varying nucleotide sequences which associate with disease-specific nucleotide sequences of varying lengths. These disease-specific nucleotide sequences may be at least 3 nucleotides in length, and as those skilled in the art will recognize, may include portions of a genome which may span several hundred nucleotides. In the case of disease-specific nucleotide sequences found in the genome or other organelle located in a living cell, the catalytic and prodrug components may be designed to associate with intron, exon, homologous, heterologous, in-frame, out-of-frame, contiguous, noncontiguous, modified and unmodified nucleotide sequences. In the case disease-specific nucleotide sequences which are mRNA, the catalytic and prodrug components may be designed to associate with any sequence transcribed by the genomic and other organelle nucleotide sequences listed immediately above.

Experimental Evaluation of the Model System

The system was then examined for the three requisite features of nucleic acid triggered catalytic drug release: 1) that efficient and catalytic release of the drug from the prodrug only takes place in the presence of both the catalytic component and triggering sequence, 2) that the complex formed between the catalytic component and the triggering sequence behaves like an enzyme, and 3) that the rate of drug release is selective for the fully complementary triggering sequence. These features were verified by spectroscopically monitoring the release of p-nitrophenolate at 400 nm under a variety of conditions as described in the following paragraphs.

Requirement for All Three Components

Figure 4:
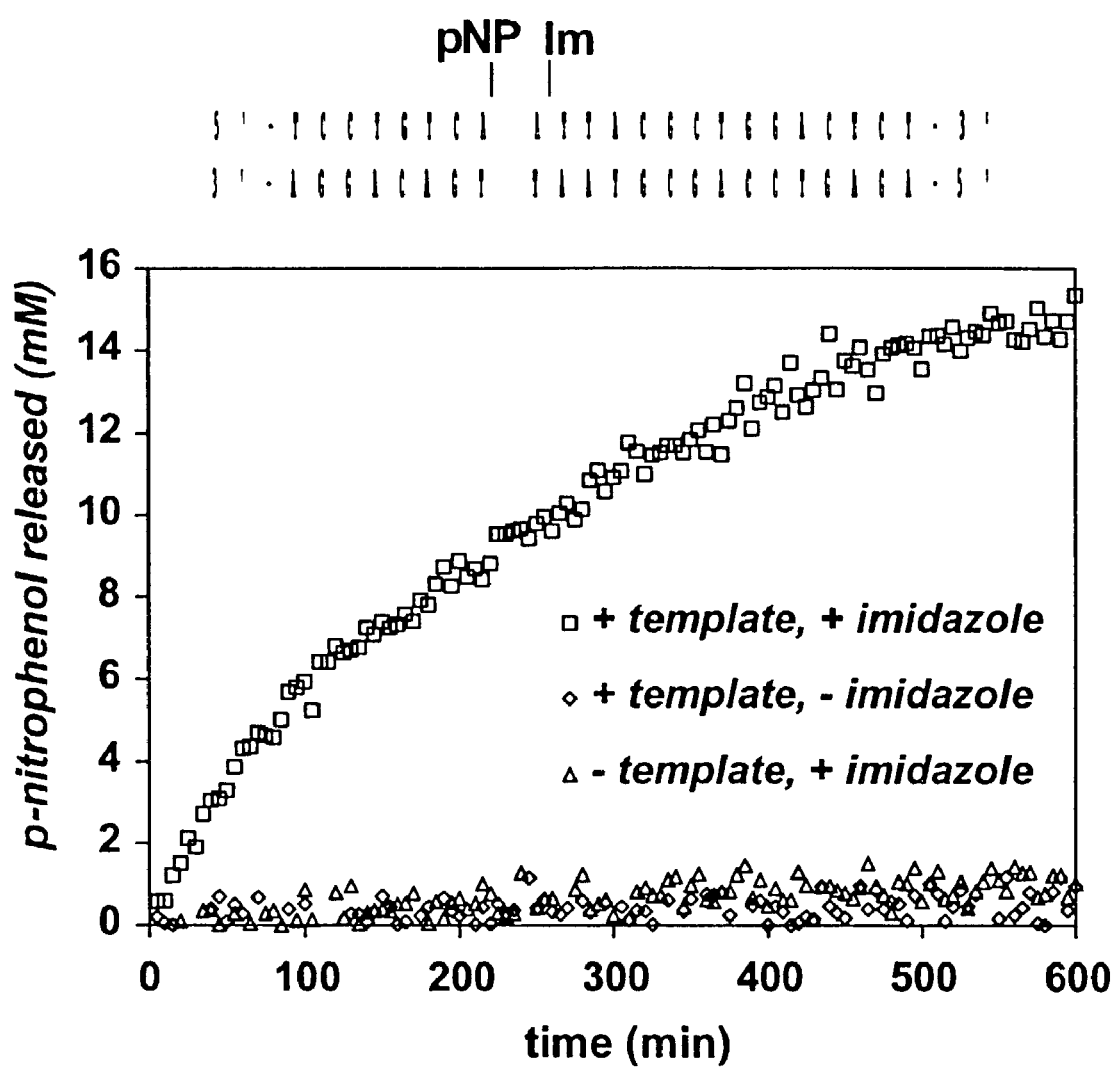
FIG. 4. Efficient and catalytic release of the drug requires both the catalytic component and the triggering sequence. Im-15-mer (SEQ ID NO:2) or the 15-mer lacking the imidazole group (5 mM) was incubated with pNP-8-mer (20 mM) (SEQ ID NO:1) at 20° C. in the presence or absence of triggering 23-mer (5 mM) (SEQ ID NO:3) in a 10 mL, 1 cm path length cell, at pH 7 in a 1 M NaCl, 10 mM sodium phosphate buffer. The release of p-nitrophenol as a function of time was monitored by UV/Vis spectroscopy at 400 nm on a Cary 1 E UV/Vis spectrophotometer and the absorbance readings converted to mM p-nitrophenol based on its molar extinction coefficient in the buffer system used. The rate of release in the absence of Im-15-mer (not shown) was similar to that observed in the absence of the 23-mer.

The requirement that both the catalytic component and triggering sequence be present for efficient drug release from the prodrug component was examined by monitoring the release of p-nitrophenol from pNP-8-mer (SEQ ID NO:1) with various combinations of Im-15-mer (SEQ ID NO:2), a 15-mer lacking the imidazole group, and the triggering 23-mer (SEQ ID NO:3) in 1 M NaCl, pH 7 at 20° C. Only when Im-15-mer (SEQ ID NO:2) and the triggering 23-mer (SEQ ID NO:3) were present did the release of p-nitrophenol occur at a significant rate above background (FIG. 4). Whereas the initial rate of p-nitrophenol release was 0.057 mM/min in the presence of all three components, it was 0.002 mM/min in the absence of the 23-mer (SEQ ID NO:3) or Im-15-mer (SEQ ID NO:2), and 0.0008 mM/min in the presence of a 15-mer lacking an appended imidazole group. Most significantly, p-nitrophenol was released catalytically as evidenced by the formation of about 15 mM p-nitrophenol during the course of the reaction in the presence of only 5 mM of the catalytic ODN and 5 mM of the triggering ODN.

Enzyme-Like Behavior

The expectation that the complex formed between the catalytic component and the triggering sequence should behave like an enzyme was investigated by determining the initial rate of drug release as a function of substrate concentration and a competitor ODN (FIG. 5). As expected for an enzyme-like system, release of p-nitrophenol from pNP-8-mer (SEQ ID NO:1) was found to follow simple Michaelis-Menten kinetics (FIG. 4), with a $V_{max}$ of 0.09 mM min$^{-1}$ ($k_{cat}$ of 0.018 min$^{-1}$) and a $K_M$ of 22 mM. This corresponds to a 976-fold rate acceleration over the hydrolysis of the p-nitrophenyl ester of valine maleimide 8 catalyzed by free imidazole ($k_{Im}$=0.014 M$^{-1}$ s$^{-1}$) as calculated by ($k_{cat}/K_M$)/$k_{Im}$. In a study of a relate system in which the valine ester was replaced by a b-aminopropionate ester, $k_{cat}$ was 10-fold higher (data not shown), indicating that the reaction is quite sensitive to the presence of a-substituents, as has been found for other p-nitrophenyl esters. To further investigate the analogy with an enzymatic system, we examined the effect of adding an 8-mer lacking the p-nitrophenylester group on the rate of p-nitrophenol release and found that it behaves like a competitive inhibitor with a $K_I$ of 1.7 mM.

Sensitivity to Mismatches

The requirement that drug release is selective for the fully complementary triggering sequence was tested by monitoring the release of p-nitrophenol from pNP-8-mer (SEQ ID NO:1) in the presence of the fully complementary 23-mer or one in which the T at position 20 was replaced with a C (FIG. 6). Release of p-nitrophenol was 7.5-fold more efficient in the presence of the fully matched template than the mismatched template at 20° C. and a physiologically relevant salt concentration of 0.1 M NaCl. Under these conditions the initial rate of release of p-nitrophenol was 0.028 mM/min in the presence of the fully matched sequence, but only 0.0037 mM/min in the presence of the mismatched sequence. These results are consistent with the prediction that the $T_M$ for the matched duplex d(TCCTGTCA).d(TGACAGGA) (SEQ ID NOS: 1and 20 respectivly) under these conditions is 34° C., whereas that of the corresponding duplex containing the TC mismatch is only 6° C. (16, 32, 33). At a higher salt concentration of 1 M NaCl, there was only a 1.4-fold difference in rate, which was consistent with the predicted $T_M$ values of 44° C. and 18° C. for the matched and mismatched duplexes, respectively. These results suggest that the selectivity of drug release for a given triggering sequence may be optimized by changing the length or other properties of the prodrug so as to optimize the differences in stability between the matched and mismatched duplexes.

Pharmaceutical Preparations and Methods of Administration

The identified compounds treat, inhibit and/or prevent diseases in subjects caused by a predetermined nucleotide sequence specific to the disease can be administered to a subject at therapeutically effective doses to treat or ameliorate the disease. A therapeutically effective dose refers to that amount of the compound sufficient to result in amelioration of symptoms of the disease caused by a predetermined nucleotide sequence specific to the disease.

Therapeutically Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$, (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans, zoo mammals, domestic livestock mammals, companion mammals and/or a laboratory mammal species. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Conclusion

We have demonstrated that genetic information can be used to trigger the catalytic release of a drug in a highly sequence specific manner by an approach which may be used to selectively kill disease-causing organisms or diseased cells. Most significantly, catalytic drug release was shown to be sensitive to even a single base pair mismatch, suggesting that this approach may be used against diseases like cancer, in which there may only be a single base-pair difference between the cancer cell and a normal cell. The ability to discriminate between nucleic acids differing in a single base is not a requirement for treating cancer, however, as one may make use of a over-expressed mRNA unique to the cancer as a trigger. This same approach could also be used for the cell-specific release of therapeutically useful drugs for other types of diseases, or for the creation of in vitro or in vivo diagnostic agents, in which genetic information is used to trigger the release of reporter molecules.

The following examples are intended to provide illustrations of the application of the present invention. The examples are not intended to completely define or otherwise limit the scope of the invention.

EXAMPLE 1

Materials and Methods

Dichloromethane and triethylamine were dried by refluxing with $CaH_2$ overnight followed by distillation. Histamine, maleic anhydride, and thionyl chloride were purchased from Aldrich. Tris(2-carboxyethyl)phosphine hydrochloride (TCEP.HCl) was purchased from Pierce. Reagents for automatic oligonucleotides synthesis were purchased from Glen Research. Oligodeoxynucleotides were synthesized on an Applied Biosystems 380 DNA synthesizer using phosphoramidite chemistry and recommended protocols (DMT off synthesis). $^1H$ NMR, $^{13}C$ NMR and $^{31}P$ NMR spectra were obtained on a Varian UnityPlus-300 (300 MHz) or Varian Mercury-300 (300 MHz) spectrometers. The chemical shifts are expressed in ppm from TMS using residual chloroform (d=7.24) and acetone (d=2.04) as an internal standard. $^{31}P$ NMR spectra were referenced against 85% $H_3PO_4$ in a coaxial insert. Flash chromatography was performed on Selecto Scientific silica gel. Thin layer chromatography (TLC) was run on pre-coated 254 nm fluorescent silica gel sheets manufactured by Alltech. UV spectral data were acquired on a Bausch and Lomb Spectronic 1001 spectrophotometer or Varian Cary 1E UV-Vis Spectrophotometer. MALDI mass spectra of oligodeoxynucleotides were measured on PerSeptive Voyager RP MALDI-TOF mass spectrometer.

Synthesis of Im-15-mer 2 (SEQ ID NO:2)

Imidazole was linked to the 5'-end of d(ATTACGCTG-GACTCT) by a procedure well-known in the art. Phosphoramidite 11 was used in the last coupling step (0.1 M 11 in acetonitrile; coupling time 30 min). After oxidation with 0.1 M iodine, the protected oligodeoxynucleotide was treated with 0.2 M histamine 12 in water for 6 h. Complete deprotection was carried out in concentrated aqueous ammonia at 55° C. for 8 h. The ammonia solution was evaporated to dryness on a Savant Speedvac, first under water aspirator pressure and then under high vacuum to yield the crude oligomer 2. It was then dissolved in doubly distilled water and purified by reversed phase HPLC on a Rainin Dynamax column (C-18, 5 mm, 4.6'250 mm) using buffer A (50/50 v/v 100 mM triethyl ammonium acetate buffer pH 7.0/water) and B (50/50 v/v 100 mM triethyl ammonium acetate buffer pH 7.0/acetonitrile). A linear gradient was run from 0% to 30% B in 30 min at a flow rate of 1.0 mL/min and the effluent monitored at 260 nm. The desired fraction was collected, concentrated and desalted by loading onto the same column in pure water, washing with excess doubly distilled water, and eluting with 50:50 acetonitrile:water. The desalted fractions were combined and concentrated to dryness in vacuo. The purified product 2 was analyzed by MALDI-TOF, [M–H$^+$] 4771.8, found 4773.4.

Synthesis of Maleamic Acid of D-Valine 6

D-Valine (11.7 g, 100 mmol) was dissolved in 10 mL of water and then maleic anhydride (9.8 g, 100 mmol) was added all at once and stirred for 4 h at ambient temperature. The resulting white powder was filtered, washed with water (3'10 mL) followed by anhydrous ethanol (3'10 ml), and then anhydrous ether (3'10 mL) to give 11.6 g (69%) of the maleamic acid 6 (18). $[a]_D$=–15.0° C. (c 1.1, acetone); $^1$H NMR (300 MHz, CD$_3$COCD$_3$) d 1.01 (d, J=4.9 Hz, 6H) 2.05 (m, 1H), 4.53 (m, 1H), 6.32 (d, J=12.9 Hz, 1H), 6.76 (d, J=12.9 Hz, 1H).

Synthesis of N-maleoyl-D-valine ester 8

The maleamic acid of D-valine 6 (500 mg, 2.54 mmol) was dissolved in 10 mL of thionyl chloride and heated at reflux until gas evolution had ceased. The excess thionyl chloride was evaporated under reduced pressure. Carbon tetrachloride was added to the remaining material, and the resulting solution was evaporated under reduced pressure to insure complete removal of thionyl chloride. The resulting product was dissolved in 10 mL of CH$_2$Cl$_2$ and was slowly added to a stirred mixture of 4-nitrophenol 7 (353 mg, 2.54 mmol) and triethylamine (0.71 mL, 5.08 mmol) in 10 mL of CH$_2$Cl$_2$ at 0° C. The reaction mixture was allowed to warm to room temperature. After stirring an additional one-half hour at room temperature, the reaction mixture was diluted with 200 mL CH$_2$Cl$_2$, washed with brine, water, dried over Na$_2$SO$_4$ and concentrated in vacuo. The residue was flash chromatographed on silica gel (1:4 ethyl acetate:hexane) to afford the N-maleoyl-D-valine ester 8, 246 mg (33%). $[a]_D$=+33.0° (c 0.9, acetone); $^1$H NMR (300 MHz, CD$_3$COCD$_3$) d 0.93 (d, J=6.6 Hz, 3H), 1.11 (d, J=6.8 Hz, 3H), 2.60~2.64 (m, 1H), 4.82 (d, J=7.1 Hz, 1H), 7.05 (s, 2H),7.36~7.39 (m, 2H), 8.30~8.32 (m, 2H); $^{13}$C NMR (300 MHz, CD$_3$COCD$_3$) d 19.9, 20.8, 57.2, 123.6, 123.8, 125.8, 135.3, 146.3, 156.0, 167.4, 170.9; HRMS calcd. for C$_{15}$H$_{15}$N$_2$O$_6$ [M+H$^+$] 319.0930, found 319.0931.

Synthesis of pNP-8-mer 1

The conjugation of a 3'-thiolated ODN with a maleimide group was carried out according to a general procedure. The ODN 9 bearing a 3'-terminal disulfide group (100 nmol) (20) was reduced to one with a 3'-terminal thiol group 10 with Tris(2-carboxyethyl)phosphine (TCEP) (150 nmol) in 500 mL 0.1 M sodium phosphate buffer, pH 7.0, for 2 h at RT under argon. The N-maleoyl-D-valine ester 8 (1 mmol, in 50 mL acetonitrile) was then added to 10 to give pNP-8-mer 1 which was purified by reversed phase HPLC on a Rainin Dynamax column (C-18, 5 mm, 4.6'250 mm) using buffers A (90/10 v/v 75 mM sodium phosphate buffer pH 7.0/10% methanol) and B (50/50 75 mM sodium phosphate buffer pH 7.0/methanol). A 30 min 1 mL/min linear gradient was run from 0% to 100% B in A and the effluent monitored at 260 nm. The desired fraction was collected, concentrated and desalted by loading onto the same column, washing with excess doubly distilled water and eluting with 50/50 acetonitrile/water. The desalted fractions were combined and concentrated to dryness in vacuo. The product was analyzed by MALDI-TOF, calcd [M–H$^+$] 2803.2, found 2802.9.

Kinetics

For typical assays, pNP-8-mer 1 (SEQ ID NO:1) and Im-15-mer 2 were incubated in 10 mM sodium phosphate, pH 7.0, which contained 0.1 M or 1.0 M NaCl in an ultra-micro (10 mL) UV cell (Varian). The reaction temperature was maintained at 20° C., and the production of p-nitrophenolate was monitored by UV absorbance at 400 nm (e$_{400}$=6.26'10$^3$). Initial velocities of the reaction, obtained for each substrate concentration, were fitted to the Michaelis-Menten equation by a non-linear least squares method with KaleidaGraph software. The inhibition constant K$_I$ was determined in the presence of 20 mM d(TCCTGTCA) in 10 mM sodium phosphate buffer pH 7.0 containing 1.0 M NaCl by the plotting 1/v vs. 1/[S] and calculating K$_I$ from the slope of the line according following equation:

$$\frac{1}{v} = \frac{1}{V_{max}} + \frac{K_M\left(1 + \frac{[I]}{K_I}\right)}{V_{max}} \times \frac{1}{[S]}$$

where v is the velocity of the reaction, V$_{max}$ is the maximum velocity, K$_M$ is the substrate concentration at half maximal reaction rate, [I] is the inhibitor concentration, and [S] is the substrate concentration. For comparison purposes, the reaction rate constant k$_{Im}$ for the imidazole catalyzed hydrolysis of N-maleoyl-D-valine p-nitrophenyl ester 8 was determined in imidazole buffer at pH 7.0, 1.0 M NaCl at 20° C. as previously described.

EXAMPLE 2

Materials and Methods

Dichloromethane and triethylamine were dried by refluxing with CaH$_2$ overnight followed by distillation. Benzyl mercaptan, dimethylaminopyridine (DMAP), 1,3-dicyclohexylcarbodiimide (DCC), dichloroacetic acid, 2-(cyanoethyl)-N,N,N',N'-tetraisopropylphosphorodiamidite, histamine, maleic anhydride, thionyl chloride and b-alanine were purchased from Aldrich. Tris(2-carboxyethyl)phosphine hydrochloride (TCEP.HCl) was purchased from Pierce. Reagents for automatic oligonucleotides synthesis were purchased from Glen Research. Oligonucleotides were assembled on an Applied Biosystems 380 DNA synthesizer using phosphoramidite chemistry and recommended protocols (DMTr off synthesis). Oligonucleotides were purified by reversed phase HPLC as described below in detail. $^1$H NMR, $^{13}$C NMR and $^{31}$P NMR spectra were obtained on either a Varian UnityPlus-300 (300 MHz) or Varian Mercury-300 (300 MHz) spectrometer. The chemical shifts are expressed in ppm downfield from residual chloroform (d=7.24) and acetone (d=2.04) as an internal standard. $^{31}$P NMR spectra were referenced against 85% H$_3$PO$_4$ in a coaxial insert. Flash chromatography was performed on Selecto Scientific silica gel. Thin layer chromatography (TLC) was run on pre-coated 254 nm fluorescent silica gel sheets manufactured by Alltech.

UV spectral data were acquired on a Bausch and Lomb Spectronic 1001 spectrophotometer or Varian Cary 1E UV-Vis Spectrophotometer. Fluorescence measurements were carried out on a SPEX Fluoromax instrument. MALDI mass spectra of oligodeoxynucleotides were measured on PerSeptive Voyager RP MALDI-TOF mass spectrometer.

Synthesis of the Imidazole Hairpin 3a (SEQ ID NO:4)

The oligonucleotides were assembled on commercial nucleoside derivatized columns using standard protocols. Phosphoramidite 1 (reference) was used in the last coupling step (0.1 M in acetonitrile; 30 min coupling time). After oxidation with 0.1 M iodine, the protected ODN 2a was treated with 0.2 M histamine in water for 6 h (1). Complete deprotection was carried out in concentrated aqueous ammonia at 55° C. for 8 h. The ammonia solution was evaporated to dryness on a Savant Speedvac, first under water aspirator pressure and then under high vacuum to yield the crude oligomer 3a. It was then dissolved in doubly distilled water and purified by reversed phase HPLC on a Rainin Dynamax column (C-18, 5 mm, 4.6'250 mm) using two buffers: A [100 mM triethyl ammonium acetate buffer pH 7.0(50%)/water (50%)] and B [100 mM triethyl ammonium acetate buffer pH 7.0 (50%)/acetonitrile (50%)]. A linear gradient was run from 0% to 30% B in 30 min, flow rate=1.0 mL/min. The wavelength of the detector was set at 260 nm. The pure fraction was collected, concentrated and desalted by using the same column, washed with excess doubly distilled water and eluted with 50:50 acetonitrile/water. The desalted fractions were combined and concentrated to dryness in vacuo. The product 3a was analyzed by MALDI-TOF, calcd (M−H$^+$) 7622.0, found 7621.3.

Synthesis of Fluorescein Dipivalate Oligodeoxynucleotide Conjugates 7

To a mixture of DMF (32 mL) and 0.1 M NaHCO$_3$/Na$_2$CO$_3$ buffer (pH 9) (140 mL) were added successively a solution of 3'-amino-linked oligo 5 (1.2 mM in water, 36 nmol) and a solution of the activated ester 6 (12 mM in DMF, 1.44 mmol). The turbid mixture was stirred vigorously at room temperature for 1.5 h in the dark. The oligodeoxynucleotide conjugates 7 were purified by preparative reverse-phased HPLC on a Rainin Dynamax column (solvent A=0.05 M triethylammonium acetate, pH 7; solvent B=80% acetonitrile in buffer A; linear gradient, from 7% to 63% of B over 20 min and then to 100% of B over 20 min; flow rate=1 mL min$^{-1}$). Yield (measured by UV absorbance at 260 nm) was 25% after purification. The conjugates were analyzed by MALDI-MS m/z [M−H] 7a: calcd. 1910.5, obsd. 1909.2; 7b: calcd. 2503.9, obsd. 2502.5; 7c: calcd. 3097.3, obsd. 3095.8.

Synthesis of the Maleamic Acid of b-alanine 8 b-Alanine (8.9 g, 100 mmol) was dissolved in 10 mL of water. Maleic anhydride (9.8 g, 100 mmol) was added all at once and the mixture was stirred for 4 hours at ambient temperature. After completion of the reaction, the mixture was filtered and the white power obtained was washed with water (3'10 mL) followed by anhydrous ethanol (3'10 ml), and then anhydrous ether (3'10 mL). After drying, 11.6 g (69%) of the maleamic acid was obtained. $^1$H NMR (300 MHz, D$_2$O) d 2.45 (t, J=6.4 Hz, 2H), 3.32 (t, J=6.4 Hz, 2H), 6.06 (d, J=12.4 Hz, 1H), 6.26 (d, J=12.4 Hz, 1H); HRMS (FAB) calcd for C$_7$H$_{10}$NO$_5$ (M+H$^+$) 188.0559, found 188.0558.

Synthesis of N-maleoyl-b-Alanine-4-nitrophenol ester 9a

The maleic acid 6 was dissolved in 20 mL of thionyl chloride and heated at reflux until gas evolution had ceased. The excess thionyl chloride was evaporated under reduced pressure. Carbon tetrachloride was added to the remaining material, and the resulting solution was evaporated under reduced pressure to insure complete removal of thionyl chloride. The resulting product was dissolved in 20 mL of CH$_2$Cl$_2$ and was slowly added to a stirred mixture of 4-nitrophenol (0.82 g, 5.9 mmol) and triethylamine (1.6 mL, 12 mmol) in 20 mL of CH$_2$Cl$_2$ at 0° C. The reaction mixture was allowed to warm to room temperature. After stirring an additional one-half hour at room temperature, the reaction mixture was diluted with 200 mL CH$_2$Cl$_2$, washed with brine, water, dried over Na$_2$SO$_4$ and concentrated in vacuo. The residue was recrystallized in ethyl acetate and hexane mixture (v/v=1:1) to afford the ester 9a, 1.5 g (88%). $^1$H NMR (300 MHz, CDCl$_3$) d 2.92 (t, J=6.9 Hz, 2H), 3.98 (t, J=6.9 Hz, 2 H), 6.74 (s, 2H), 7.30 (d, J=9.0 Hz, 2H), 8.26 (d, J=9.0 Hz, 2H); $^{13}$C NMR (300 MHz, CDCl$_3$) d 33.3, 33.4, 122.5, 125.2, 134.3, 145.4, 155.0, 168.4, 170.2; HRMS calcd for C$_{13}$H$_{10}$N$_2$O$_6$Na (M+Na$^+$) 313.0436, found 313.0439.

Synthesis of N-maleoyl-b-alanine-coumarin ester 9c

The maleamic acid of b-alanine 8 (475 mg, 2.54 mmol) was dissolved in 6 mL of thionyl chloride and heated at reflux until gas evolution had ceased. The excess thionyl chloride was evaporated under reduced pressure. Carbon tetrachloride was added to the remaining material, and the resulting solution was evaporated under reduced pressure to insure complete removal of thionyl chloride. The resulting product was dissolved in 10 mL of THF and was slowly added to a stirred mixture of 7-hydroxycoumarin (411 mg, 2.54 mmol) and triethylamine (0.74 mL, 5.36 mmol) in 20 mL of THF at 0° C. The reaction mixture was allowed to warm to room temperature. After stirring an additional one-half hour at room temperature, the reaction mixture was diluted with 200 mL ethyl acetate, washed with brine, water, dried over Na$_2$SO$_4$ and concentrated in vacuo. The residue was flash chromatographed on silica gel (1:1 ethyl acetate:hexane) to afford the N-maleoyl-b-alanine ester 9c, 300 mg (38%). $^1$H NMR (300 MHz, CDCl$_3$) d 2.92 (t, J=6.6 Hz, 2H), 3.97 (t, J=6.98 Hz, 2H), 6.41 (d, J=9.6 Hz, 1H), 6.76 (s, 2H), 7.06~7.10 (m, 1H), 7.14 (d, J=2.2 Hz, 1H), 7.50 (d, J=8.2 Hz, 1H), 7.70 (d, J=9.3 Hz, 1H).

Synthesis of N-maleoyl-D-valine-2-nitrophenol ester D-11b

The maleamic acid of D-valine 10 (500 mg, 2.54 mmol) was dissolved in 10 mL of thionyl chloride and heated at reflux until gas evolution had ceased. The excess thionyl chloride was evaporated under reduced pressure. Carbon tetrachloride was added to the remaining material, and the resulting solution was evaporated under reduced pressure to insure complete removal of thionyl chloride. The resulting product was dissolved in 10 mL of CH$_2$Cl$_2$ and was slowly added to a stirred mixture of 2-nitrophenol (323 mg, 2.32 mmol) and triethylamine (0.64 mL, 4.64 mmol) in 10 mL of CH$_2$Cl$_2$ at 0° C. The reaction mixture was allowed to warm to room temperature. After stirring an additional one-half hour at room temperature, the reaction mixture was diluted with 200 mL CH$_2$Cl$_2$, washed with brine, water, dried over Na$_2$SO$_4$ and concentrated in vacuo. The residue was flash chromatographed on silica gel (1:4 ethyl acetate:hexane) to afford the N-maleoyl-D-valine ester D-11b, 270 mg (37%). [a]$_D$=+25.5° (c 0.94, acetone); $^1$H NMR (300 MHz, CD$_3$COCD$_3$) d 0.93 (d, J=6.9 Hz, 3H), 1.14 (d, J=6.9 Hz, 3H), 2.68~2.75 (m, 1H), 4.72 (d, J=8.0 Hz, 1H), 7.06 (s, 2H), 7.34~7.37 (m, 1H), 7.56~7.61 (m, 1H), 7.81~7.87 (m, 1H), 8.14~8.17 (m, 1H); $^{13}$C NMR (300 MHz, CD$_3$COCD$_3$) d 18.6, 20.2, 57.2, 125.3, 125.8, 127.6, 134.8, 135.3, 143.4, 166.5, 170.2.

Synthesis of N-maleoyl-D-valine coumarin ester D-11c

The maleamic acid of D-valine 8 (500 mg, 2.54 mmol) was dissolved in 10 mL of thionyl chloride and heated at reflux until gas evolution had ceased. The excess thionyl chloride was evaporated under reduced pressure. Carbon tetrachloride was added to the remaining material, and the resulting solution was evaporated under reduced pressure to insure complete removal of thionyl chloride. The resulting product was dissolved in 10 mL of $CH_2Cl_2$ and was slowly added to a stirred mixture of 7-hydroxycoumarin (376 mg, 2.32 mmol) and triethylamine (0.64 mL, 4.64 mmol) in 10 mL of $CH_2Cl_2$ at 0° C. The reaction mixture was allowed to warm to room temperature. After stirring an additional one-half hour at room temperature, the reaction mixture was diluted with 200 mL $CH_2Cl_2$, washed with brine, water, dried over $Na_2SO_4$ and concentrated in vacuo. The residue was flash chromatographed on silica gel (1:2 ethyl acetate:hexane) to afford the N-maleoyl-D-valine ester D-11c, 390 mg (49%). $[a]_D$=+ 85.2° (c 1.0, acetone); $^1$H NMR (300 MHz, $CD_3COCD_3$) d 0.93 (d, J=6.8 Hz, 3H), 1.11 (d, J=6.8 Hz, 3H), 2.60~2.64 (m, 1H), 4.79 (d, J=6.9 Hz, 1H), 6.40 (d, J=9.6 Hz, 1H), 7.05~7.10 (m, 4H), 7.72 (d, J=8.2 Hz, 1H), 7.99 (d, J=9.6 Hz, 1H); $^{13}$C NMR (75 MHz, $CD_3COCD_3$) d 19.0, 20.8, 57.3, 110.8, 116.8, 118.0, 119.1, 130.0, 135.5, 144.0, 153.8, 155.5, 160.1, 167.8, 171.2, 205.9, 206.2; HRMS (FAB) calcd for $C_{18}H_{16}NO_6$ [M+H$^+$] 342.0978, found 342.0964.

Synthesis of N-maleoyl-L-valine coumarin ester L-11c

This was prepared in 44% yield by the same method described for the D-valine derivative, D-11c.$[a]_D$=83.5° (c 1.0, acetone). General method for synthesis of the ester oligodeoxynucleotide conjugates 15 & 16 Oligodeoxynucleotide 14 (100 nmol) bearing a disulfide group (4) was reduced with TCEP (150 nmol) in 500 mL 0.1 M sodium phosphate buffer, pH 7.0, for 2 h at room temperature under argon. Maleimide ester (1 mmol in 50 mL acetonitrile) was added without elimination of the TCEP excess. The oligodeoxynucleotide conjugates were purified by reversed phase HPLC on a Rainin Dynamax column (C-18, 5 mm, 4.6'250 mm) using two buffers: A [10% methanol and 90% 75 mM sodium phosphate buffer pH 7.0] and B [50% methanol and 50% 75 mM sodium phosphate buffer pH 7.0]. A linear gradient was run from 0% to 100% B in 30 min, flow rate=1.0 mL/min and the effluent was monitored by its absorbance at 260 nm. The desired fraction was collected, concentrated and desalted by using the same column, washed with excess doubly distilled water and eluted with 50:50 acetonitrile/water. The desalted fractions were combined and concentrated to dryness in vacuo. The product was analyzed by MALDI-TOF, 15a calcd (M–H$^+$) 2803.2, found 2802.9; 16c calcd (M=H$^+$) 2831.3, found 2832.6; 16c calcd (M–H$^+$) 2853.4, found 2852.6.

Kinetics of p-nitrophenol and 7-hydroxycoumarin Release from the Hairpin and 3-Component Systems For typical assays, phenol or coumarin oligodeoxynucleotide conjugates 15 or 16 and the imidazole hairpin 3a or the complex 3b/4 were incubated in 10 mM sodium phosphate, pH 7.0, which contained 0.1 M or 1.0 M NaCl. The reaction temperature was maintained at 20° C., and the production of phenolate or 7-hydroxycoumarin was monitored by UV absorbance at 400 nm ($e_{400}$=6.26'10$^3$ at pH 7) or by fluorescence ($I_{Ex}$=355 nm, $I_{Em}$=452 nm). Initial velocities of the reaction, obtained for each substrate concentration, were fitted to the Michaelis-Menten equation by a non-linear least squares method using KaleidaGraph software. The inhibition constant $K_I$ was determined in the presence of 25 mM 7d (TCCTGTCA) in 10 mM sodium phosphate buffer pH 7.0 containing 1.0 M NaCl by the plotting 1/v vs. 1/[S] and calculating $K_I$ from the slope of the line according following equation:

$$\frac{1}{v} = \frac{1}{V_{max}} + \frac{K_M\left(1 + \frac{[I]}{K_I}\right)}{V_{max}} \times \frac{1}{[S]}$$

where v is the velocity of the reaction, $V_{max}$ is the maximum velocity, $K_M$ is the substrate concentration at half maximal reaction rate, [I] is the inhibitor concentration, and [S] is the substrate concentration.

Kinetics of p-nitrophenol and 7-hydroxycoumarin Release by Imidazole Alone

For comparison purposes, the rate constant $k_{Im}$ for the imidazole catalyzed hydrolysis of the various esters were determined in imidazole buffer at pH 7.0, 0.5 M NaCl at 20° C. as previously described. The imidazole buffers were prepared in 0.5 M NaCl, and adjusted to pH 7 by addition of 1 M HCl. The hydrolysis reaction was followed by monitoring the absorbance of the phenolate ion at 400 nm or the fluorescence emission of 7-hydroxycoumarin at 452 nm ($I_{Ex}$=350 nm) as a function of time. In a typical run, 5 mL of the ester (8 mM in acetonitrile for the phenyl esters and 200 mM in acetonitrile for the 7-hydroxycoumarin esters) were added to a cuvette containing 400 mL of imidazole buffer (0.004 M~0.6 M), capped and mixed by inverting several times. The pseudo first-order rate constant for each concentration of imidazole was obtained by linear least squares fitting of $\ln(A_\Psi$-A) or $\ln(F_\Psi$-F) vs. time. The rate constants were then plotted against total imidazole concentration to get $k_o$, the first order rate constant for the uncatalyzed hydrolysis reaction, and $k_{Im}$, the second-order rate constant for catalysis by imidazole buffer.

Hydrolysis of Esters in Human Serum

The hydrolysis of the coumarin esters 9c, 11c, 12c, and 13c was followed in a SPEX Fluoromax spectrofluorimeter at the following wavelengths: $I_{Ex}$=350 nm, $I_{Em}$=452 nm. In a typical run, 3 mL of coumarin ester solution (7 mM in acetonitrile) was added to 400 mL of Human serum, pH 8.3 (Innovative Research Inc.) in cuvette. The cuvette was capped, inverted several times for thorough mixing, placed in a cell block and recording was begun. The appearance of 7-hydroxycoumarin was monitored at 452 nm at room temperature. The same procedure was followed for monitoring the hydrolysis of the o-nitrophenyl ester 11b except that the solution was centrifuged in an Eppendorf centrifuge prior to making absorbance measurements at 400 nm.

TABLE 1

Kinetic parameters for two component system consisting of the 8-mer prodrugs 15a (X = G), 16a, or 16c (SEQ ID NO:10) and the hairpin enzyme 3a (SEQ ID NO:4) at 20° C., in 10 mM phosphate buffer pH 7.0.

|  | b-Alanine-p-nitrophenyl ester 15a (X = G) 1.0 M NaCl | b-alanine-p-nitrophenyl ester 15a (X = G) 0.1 M NaCl | D-Valine-p-nitrophenyl ester 16a 1.0 M NaCl | D-Valine hydroxy coumarin ester 16c 1.0 M NaCl |
|---|---|---|---|---|
| $V_{max}$ (mM/s) | 1.4 ± 0.1 ' 10$^{-2}$ | 1.5 ± 0.1 ' 10$^{-2}$ | 1.7 ± 0.2 ' 10$^{-3}$ | 2.22 ± 0.05 ' 10$^{-4}$ |
| $K_m$ (mM) | 50 ± 7 | 82 ± 15 | 57 ± 13 | 16 ± 1 |

TABLE 1-continued

Kinetic parameters for two component system consisting of the 8-mer prodrugs 15a (X = G), 16a, or 16c (SEQ ID NO:10) and the hairpin enzyme 3a (SEQ ID NO:4) at 20° C., in 10 mM phosphate buffer pH 7.0.

|  | b-Alanine-p-nitrophenyl ester 15a (X = G) 1.0 M NaCl | b-alanine-p-nitrophenyl ester 15a (X = G) 0.1 M NaCl | D-Valine-p-nitrophenyl ester 16a 1.0 M NaCl | D-Valine hydroxy coumarin ester 16c 1.0 M NaCl |
|---|---|---|---|---|
| $k_{cat}\ (s^{-1})$ | $2.9 \pm 0.2 \cdot 10^{-3}$ | $3.0 \pm 0.2 \cdot 10^{-3}$ | $3.5 \pm 0.4 \cdot 10^{-4}$ | $4.4 \pm 0.1 \cdot 10^{-5}$ |
| $K_I\ (mM)$ | $38 \pm 3$ | ND | ND | ND |
| $k_{lm}\ (M^{-1} \cdot s^{-1})$ | $1.3^1 \cdot 10^{-1}$ | $1.3^1 \cdot 10^{-1}$ | $1.4 \pm 0.04 \cdot 10^{-2}$ | $1.13 \pm 0.07 \cdot 10^{-3}$ |
| Enhancement | 446 | 281 | 429 | 2,433 |

[1] For p-nitrophenylacetate.

TABLE 2

Kinetic parameters for the imidazole catalyzed hydrolysis of p-nitrophenyl and 3-hydroxycoumarin esters at pH 7 in 0.5 M NaCl at 20° C., where $k_o$ is the background hydrolysis rate constant, and $k_{lm}$ is the imidazole catalyzed rate constant.

| Ester | $k_o\ (s^{-1})$ | $k_{lm}\ (M^{-1}s^{-1})$ |
|---|---|---|
| p-nitrophenylacetate | $4.4 \cdot 10^{-5}$ | 0.13 |
| Mal-D-valine-p-nitrophenylacetate, 11a | $4.1 \pm 2 \cdot 10^{-6}$ | $1.4 \pm 0.04 \cdot 10^{-2}$ |
| Mal-D-glycine-coumarin, 12c | $1.3 \pm 6 \cdot 10^{-4}$ | $7.9 \pm 0.1 \cdot 10^{-2}$ |
| Mal-b-alanine-coumarin, 9c | $2.1 \pm 2 \cdot 10^{-5}$ | $5.7 \pm 0.05 \cdot 10^{-2}$ |
| Mal-D-valine-coumarin, 11c | $4.9 \pm 4 \cdot 10^{-7}$ | $1.13 \pm 0.07 \cdot 10^{-3}$ |
| CBZ-glycine-coumarin, 13c | $1.0 \pm 5 \cdot 10^{-4}$ | $9.2 \pm 0.5 \cdot 10^{-2}$ |

TABLE 3

Kinetic parameters for three component system consisting of the 8-mer prodrug 16a or proprobe 16c (SEQ ID NO:10), 15-mer catalytic component 3b (SEQ ID NO:5), and 23-mer template 4 (SEQ ID NO:3) (X = A) in 10 mM sodium phosphate buffer, pH 7.0 at 20° C.

|  | D-valine-nitrophenylester 16a 1.0 M NaCl | D-valine-coumarin ester 16c 1.0 M NaCl |
|---|---|---|
| $V_{max}\ (mM/s)$ | $1.5 \pm 0.02 \cdot 10^{-3}$ | $1.54 \pm 0.04 \cdot 10^{-4}$ |
| $K_m\ (mM)$ | $22 \pm 1.2$ | $18 \pm 1$ |
| $k_{cat}\ (s^{-1})$ | $3.0 \pm 0.04 \cdot 10^{-4}$ | $3.08 \pm 0.08 \cdot 10^{-5}$ |
| $K_I\ (mM)$ | $1.7 \pm$ | $9 \pm 1$ |
| $k_{lm}\ (M^{-1}/s)$ | $1.4 \pm 0.04 \cdot 10^{-2}$ | $1.13 \pm 0.07 \cdot 10^{-3}$ |
| Enhancement | 974 | 1514 |

In light of the detailed description of the invention and the examples presented, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall with the spirit and scope of the following claims.

What is claimed is:

1. A complex comprising:
   a) a single-stranded target nucleic acid comprising a first target sequence and a second target sequence;
   b) a first agent comprising i) a substrate moiety and ii) a first nucleobase polymer comprising a sequence base-paired with the first target sequence; and
   c) a second agent comprising i) a catalyst moiety and ii) a second nucleobase polymer comprising a sequence base-paired with the second target sequence, wherein the catalyst moiety is adjacent to the substrate moiety, and wherein the catalyst moiety activates and/or releases the substrate moiety with multiple turnovers of the first agent, at a rate greater than that of a mixture comprising the first agent and the second agent but not the target nucleic acid.

2. A complex in accordance with claim 1, wherein the substrate moiety comprises a linker which connects to the first nucleobase polymer.

3. A complex in accordance with claim 2, wherein the linker is susceptible to cleavage by the catalyst moiety.

4. A complex in accordance with claim 1, wherein the first nucleobase polymer comprises a sequence of from 4 to 8 bases complementary to the first target sequence.

5. A complex in accordance with claim 1, wherein the first nucleobase polymer is selected from the group consisting of a tetramer, a hexamer and an octamer.

6. A complex in accordance with claim 1, wherein the first nucleobase polymer is an 8-mer.

7. A complex in accordance with claim 1, wherein the second nucleobase polymer is at least 15 nucleotides in length.

8. A complex in accordance with claim 1, wherein the first nucleobase polymer and the second nucleobase polymer are each independently selected from the group consisting of an oligodeoxynucleotide (ODN) and a peptide nucleic acid (PNA).

9. A complex in accordance with claim 1, wherein the substrate moiety is an ester of an active compound.

10. A complex in accordance with claim 9, wherein the catalyst moiety catalyzes de-esterification of the substrate moiety, thereby converting the substrate moiety to the active compound.

11. A complex in accordance with claim 10, wherein the catalyst moiety is an imidazole.

12. A complex in accordance with claim 1, wherein the substrate moiety is a prodrug.

13. A complex in accordance with claim 12, wherein the prodrug is selected from the group consisting of a hydroxymethylphenyl-based prodrug and a trimethylene lock-based prodrug.

14. A complex in accordance with claim 1, wherein the substrate moiety comprises a cytotoxic drug.

15. A complex in accordance with claim 1, wherein the substrate moiety is a fluorogenic moiety.

16. A complex in accordance with claim 15, wherein the fluorogenic moiety is selected from a fluorescein dipivalate and a hydroxycoumarin ester.

17. A complex in accordance with claim 1, wherein the substrate moiety is a chromogenic moiety.

18. A complex in accordance with claim 17, wherein the chromogenic moiety is a nitrophenyl ester.

19. A complex in accordance with claim 1, wherein the target nucleic acid is an RNA.

20. A complex in accordance with claim 19, wherein the RNA is an mRNA.

21. A method of activating and/or releasing a substrate of a catalyst, the method comprising forming a mixture comprising:
   a) a single-stranded target nucleic acid comprising a first target sequence and a second target sequence;
   b) a first agent comprising i) a substrate moiety and ii) a first nucleobase polymer comprising a sequence complementary to the first target sequence; and
   c) a second agent comprising i) a catalyst moiety and ii) a second nucleobase polymer comprising a sequence complementary to the second target sequence,
wherein the single-stranded nucleic acid, the first agent and the second agent form a complex in which the catalyst moiety is adjacent to the substrate moiety, and wherein the catalyst moiety activates and/or releases the substrate moiety with multiple turnovers, at a rate greater than that of a mixture comprising the first agent and the second agent but not the target nucleic acid.

22. A method in accordance with claim 21, wherein the substrate moiety comprises a prodrug, a cytotoxin, a fluorogen or a chromogen.

23. A method in accordance with claim 21, wherein the substrate moiety comprises a linker which connects to the first nucleobase polymer.

24. A method in accordance with claim 21, wherein the single-stranded target nucleic acid is a single-stranded RNA.

25. A method in accordance with claim 24, wherein the RNA is an mRNA.

26. A method in accordance with claim 21, wherein the target nucleic acid is comprised by a cancer cell, and the substrate moiety comprises a cytotoxin.

27. A method of detecting presence, absence or quantity of a single-stranded target nucleic acid in a sample, the method comprising:
   providing a sample comprising or suspected of comprising a single-stranded target nucleic acid;
   forming a mixture comprising the sample, a first agent comprising i) a substrate moiety and ii) a first nucleobase polymer comprising a sequence complementary to the first target sequence; and a second agent comprising i) a catalyst moiety and ii) a second nucleobase polymer comprising a sequence complementary to the second target sequence, wherein the substrate moiety is a substrate for the catalyst moiety; and
   determining the presence, absence or quantity of a compound which forms upon activation and/or release of the substrate moiety
wherein if the mixture comprises the taraet nucleic acid, the substrate moiety is activated and/or released with multiple turnovers, at a rate greater than that of a mixture comprising the first agent and the second agent but not the target nucleic acid.

28. A method of detecting presence, absence or quantity of a single-stranded target nucleic acid in accordance with claim 27, wherein the substrate moiety is comprises a fluorogenic moiety or a chromogenic moiety.

29. A method of detecting presence, absence or quantity of a single-stranded target nucleic acid in accordance with claim 28, wherein the fluorogenic moiety is selected from a fluorescein ester and a hydroxycoumarin ester.

30. A method of detecting presence, absence or quantity of a single-stranded target nucleic acid in accordance with claim 28, wherein the chromogenic moiety is a nitrophenyl moiety.

31. A complex in accordance with claim 1, wherein the first nucleobase polymer comprises a sequence which is complementary to the first target sequence in a length sufficient to insure specificity of binding to the first target sequence but which binds the first target sequence with a binding affinity sufficiently low for rapid turnover.

* * * * *

UNITED STATES PATENT AND TRADEMARK OFFICE
CERTIFICATE OF CORRECTION

PATENT NO.       : 7,445,891 B2                                Page 1 of 6
APPLICATION NO.  : 10/201680
DATED            : November 4, 2008
INVENTOR(S)      : John-Stephen Taylor It is certified that error appears in the above-identified patent and that said Letters Patent is hereby corrected as shown below:

In the drawings, Sheet 2, Figure 2 should be replaced with the following figure.

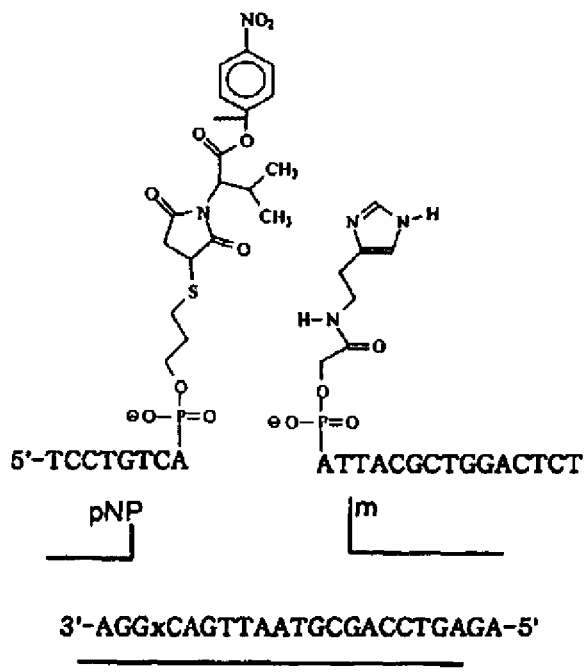

UNITED STATES PATENT AND TRADEMARK OFFICE
CERTIFICATE OF CORRECTION

PATENT NO. : 7,445,891 B2
APPLICATION NO. : 10/201680
DATED : November 4, 2008
INVENTOR(S) : John-Stephen Taylor It is certified that error appears in the above-identified patent and that said Letters Patent is hereby corrected as shown below:

In the drawings, Figure 4, Sheet 4 should be replaced with the following figure.

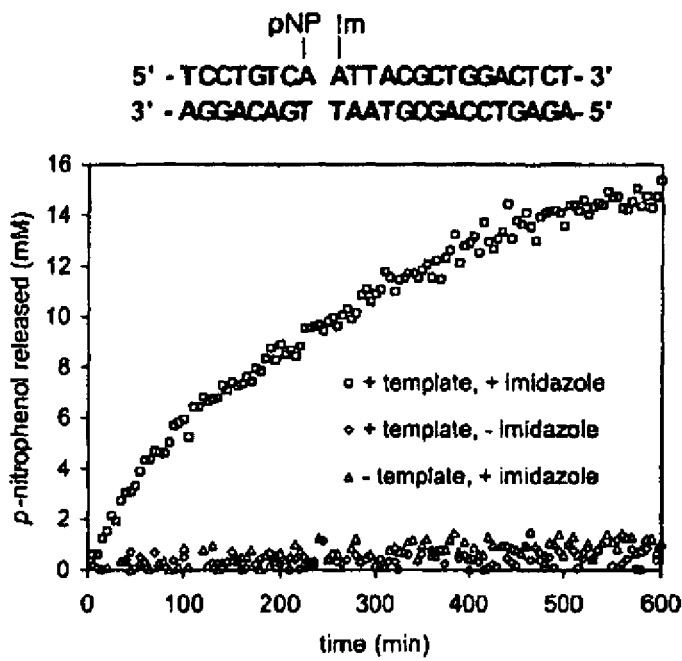

UNITED STATES PATENT AND TRADEMARK OFFICE
CERTIFICATE OF CORRECTION

PATENT NO. : 7,445,891 B2
APPLICATION NO. : 10/201680
DATED : November 4, 2008
INVENTOR(S) : John-Stephen Taylor It is certified that error appears in the above-identified patent and that said Letters Patent is hereby corrected as shown below:

In the drawings, Figure 6, Sheet 6 should be replaced with the following figure.

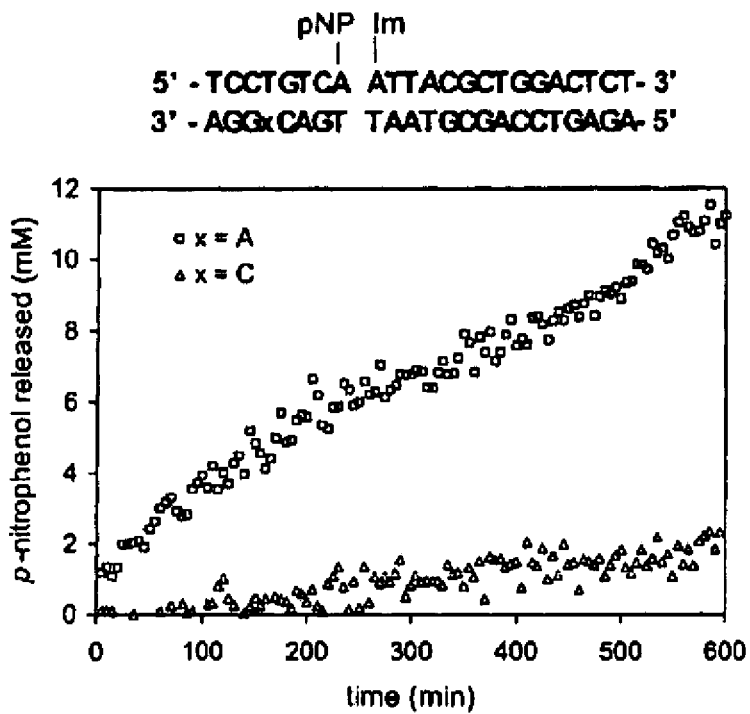

UNITED STATES PATENT AND TRADEMARK OFFICE
CERTIFICATE OF CORRECTION

| | |
|---|---|
| PATENT NO. | : 7,445,891 B2 |
| APPLICATION NO. | : 10/201680 |
| DATED | : November 4, 2008 |
| INVENTOR(S) | : John-Stephen Taylor |

It is certified that error appears in the above-identified patent and that said Letters Patent is hereby corrected as shown below:

Column 7, line 2, the figure reference "FIG. 1" should read --FIG. 7--.

Column 7, line 16, the figure reference "FIG. 2" should read --FIG. 8--.

Column 7, line 22, the figure reference "FIG. 3" should read --FIG. 9--.

Figure 10:
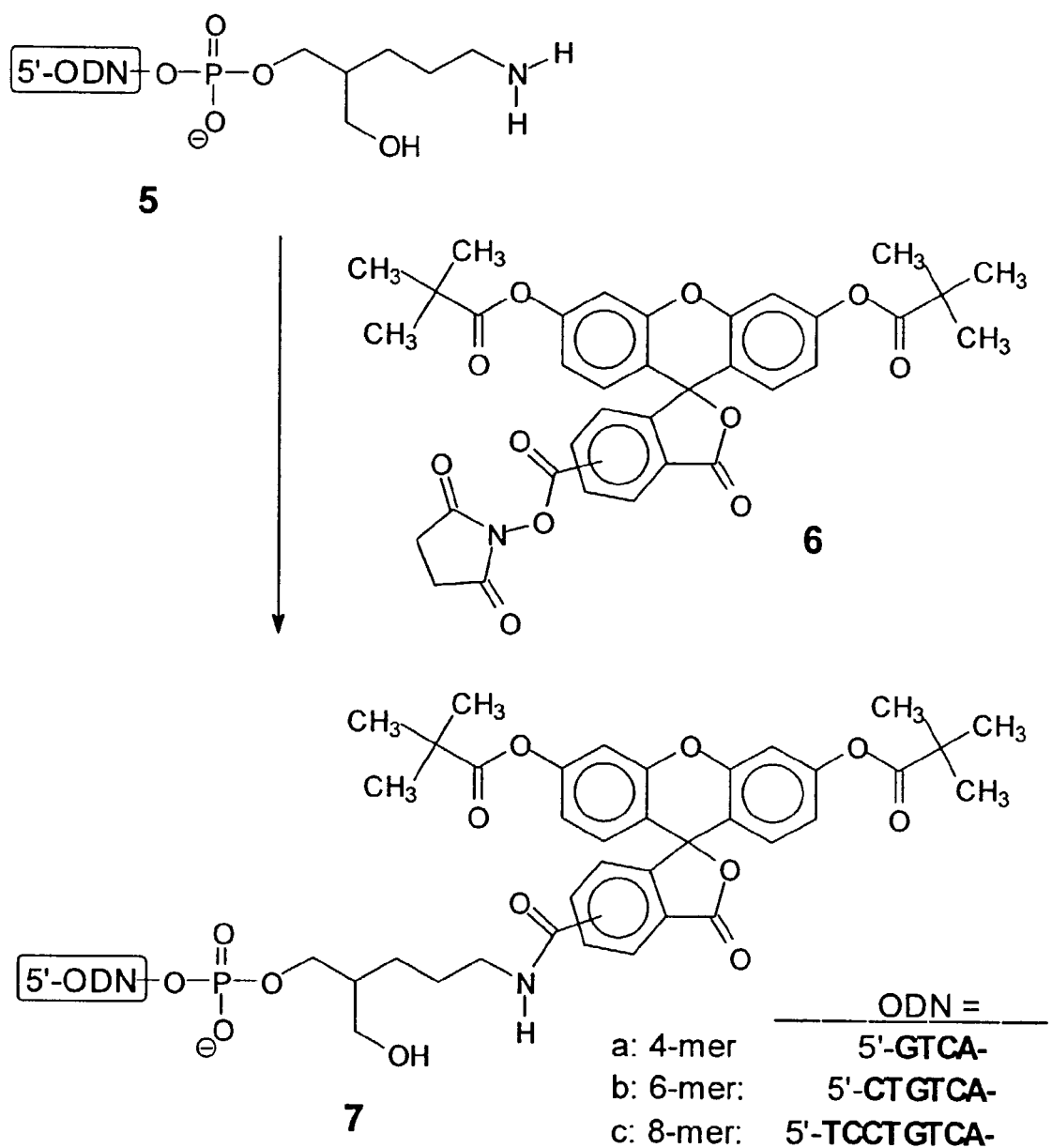
FIG. 10. Synthesis of the fluorescein dipivalate proprobes (in this case, the 4-mer represented by SEQ ID NO:7, the 8-mer represented by SEQ ID NO:8 and the 8-mer represented by SEQ ID NO:9).

Column 7, line 38, the figure reference "FIG. 4" should read --FIG. 10--.

Figure 11:
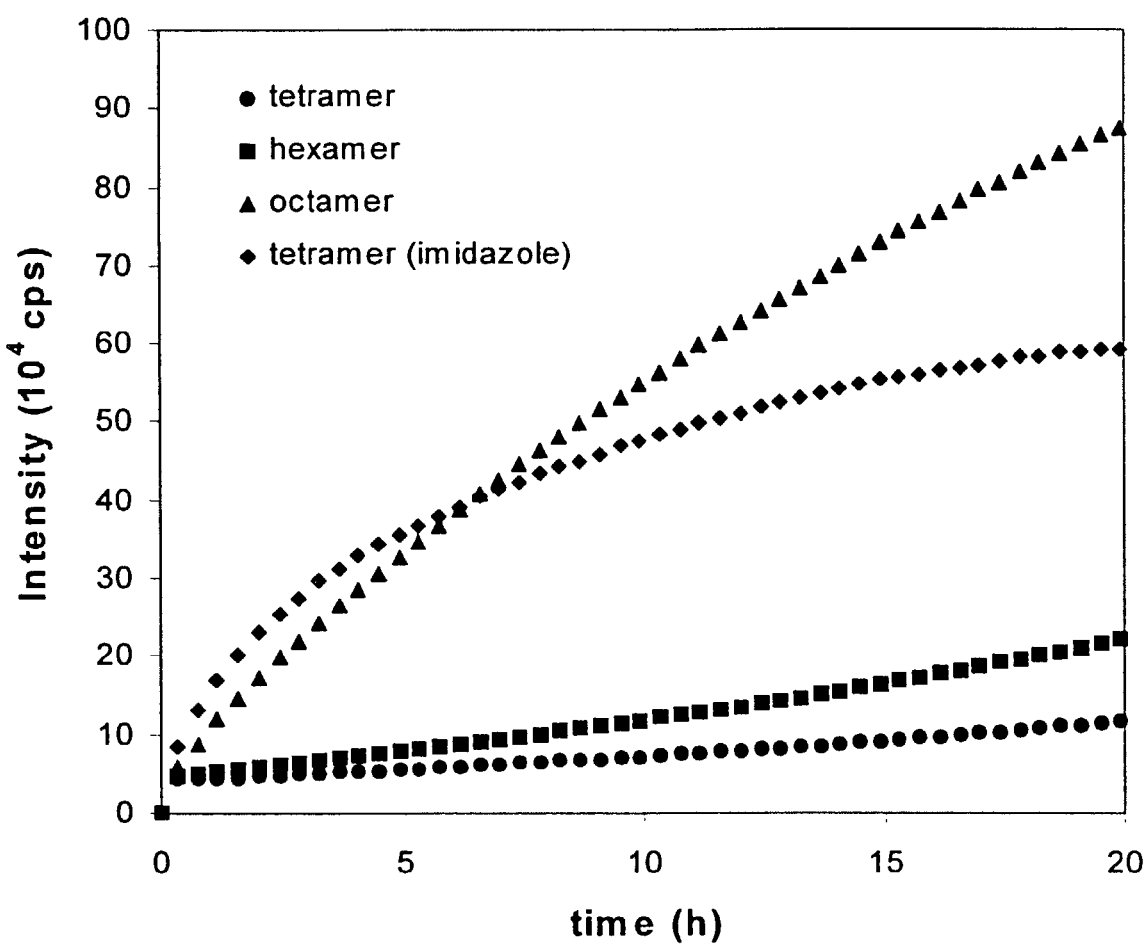
FIG. 11. Effect of oligodeoxynucleotide iength on the activation of the fluorescein dipivalate ODNs (10 mM) by the imidazole hairpin 3a(5 mM) in 0.1 M phosphate buffer (pH 7.0) at 20° C. with excitation at 490 nm and detection at 525 nm. For comparison, the release of fluorescein from the fluorescein tetramer 7a by imidazole at 0.1 M imidazole alone is also shown.

Column 7, line 56, the figure reference "FIG. 5" should read --FIG. 11--.

Column 8, line 6, "studies" should read --studied--.

Figure 12:
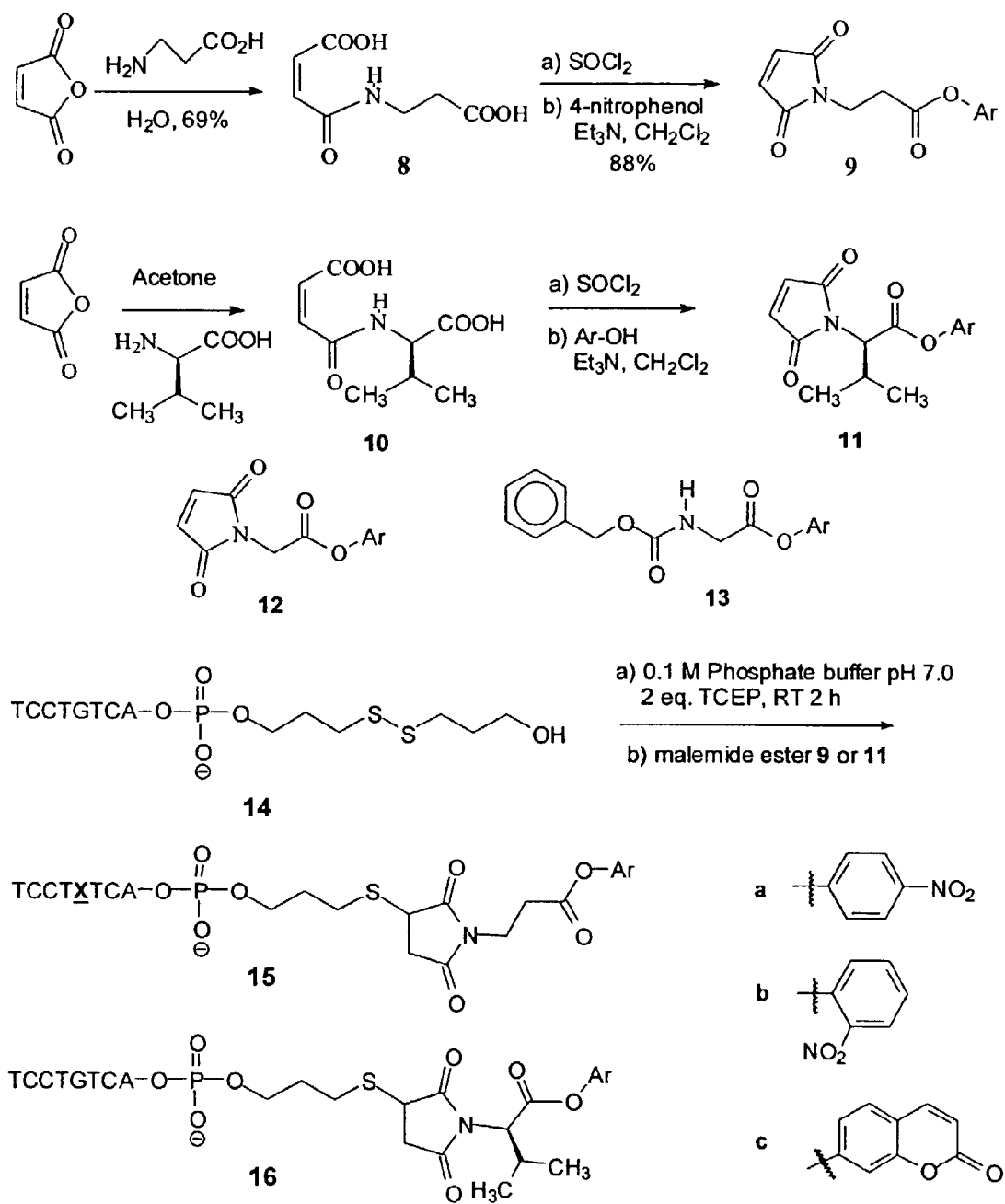
FIG. 12. Synthesis of the p-nitrophenol-based prodrugs and hydroxycourmarin-based proprobes (SEQ ID NO: 10).

Column 8, line 16 to 17, the figure reference "FIG. 6" should read --FIG. 12--.

Figure 13:
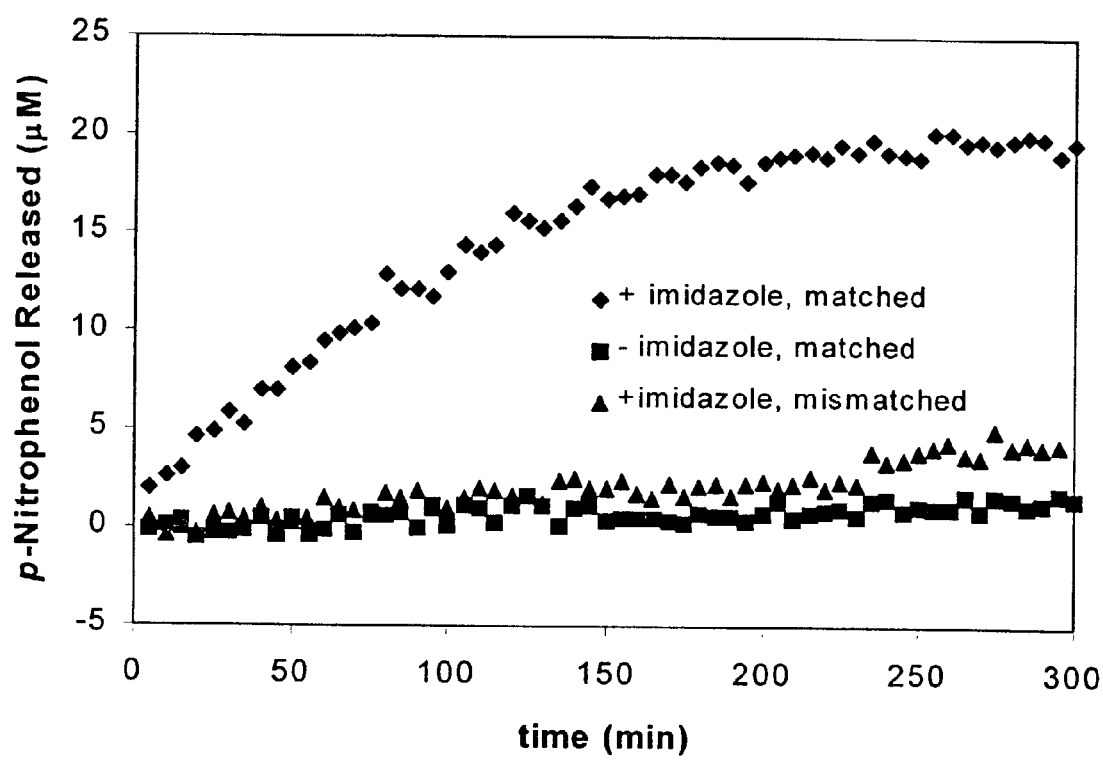
FIG. 13. Kinetics of p-nitrophenolate release from 20 mM of the matched b-alanine 8-mer prodrug 15a(X=G) in the presence of 5 mM of the imidazole hairpin 3a(+ imidazole, matched) or the hairpin lacking the imidazole group (– imidazole, matched) in 10 mM phosphate, 1 M NaCl, pH 7, at 20° C. Also shown are the kinetics of p-nitrophenolate release from the mismatched prodrug component 15a(X=C) in the presence of the imidazole hairpin 3a.(+imidazole, mismatched).

Column 8, line 28, the figure reference "FIG. 7" should read --FIG. 13--.

Figure 14:
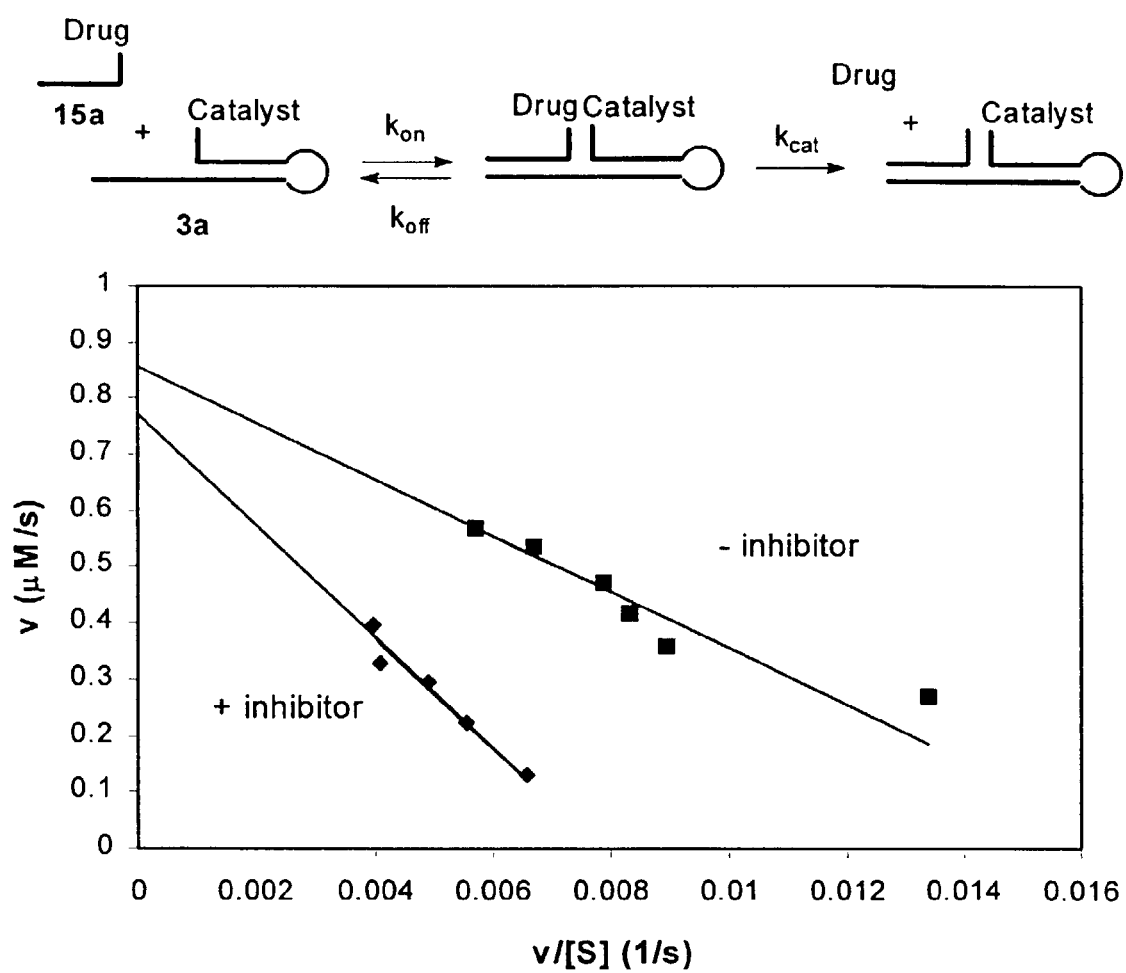
FIG. 14. Eadie-Hofstee plots of the kinetic data for p-nitrophenolate release from the matched b-alanine 8-mer prodrug 15a(X=G) by the imidazole hairpin in the presence and absence of the 8-mer inhibitor 14.

Column 8, line 34, the figure reference "FIG. 8" should read --FIG. 14--.

Column 9, line 4, the figure reference "FIG. 7" should read --FIG. 12, FIG. 13--.

Column 10, line 6, the figure reference "FIG. 6" should read --FIG. 12--.

Figure 15:
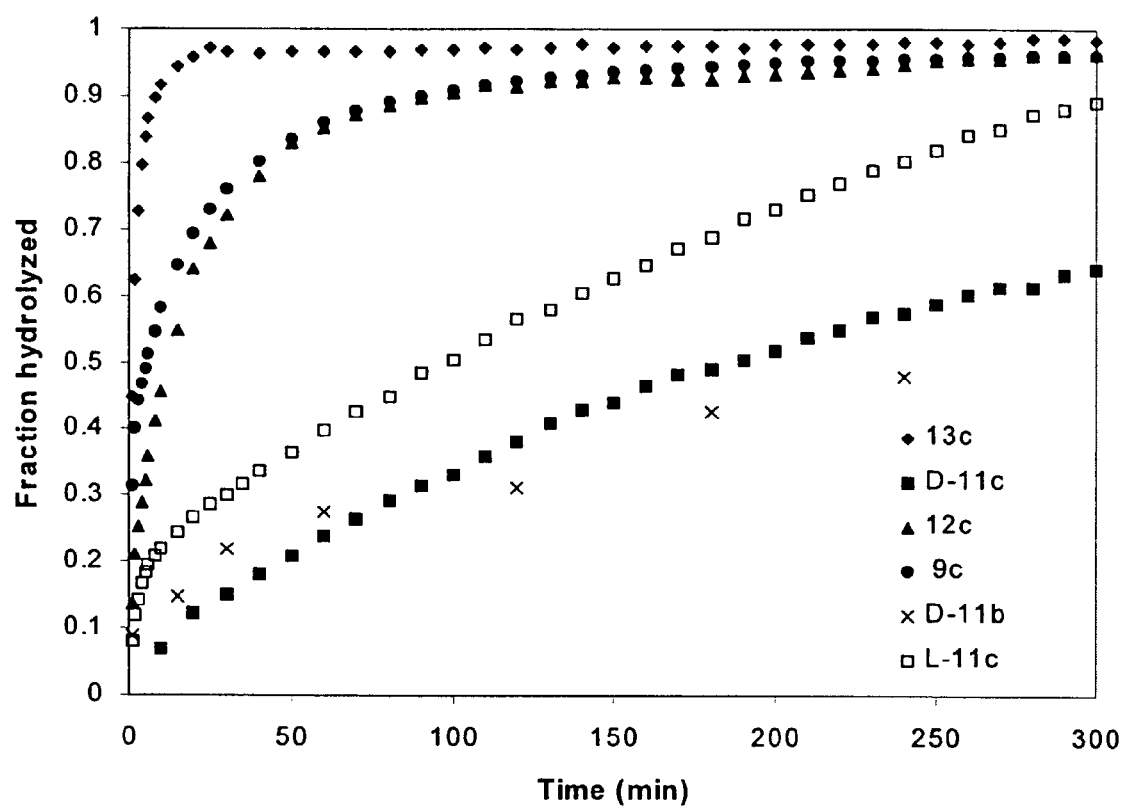
FIG. 15. Stability of various esters that could be used as prodrug linkers in human serum at 20° C. temperature at pH 8.3.
Figure 16:
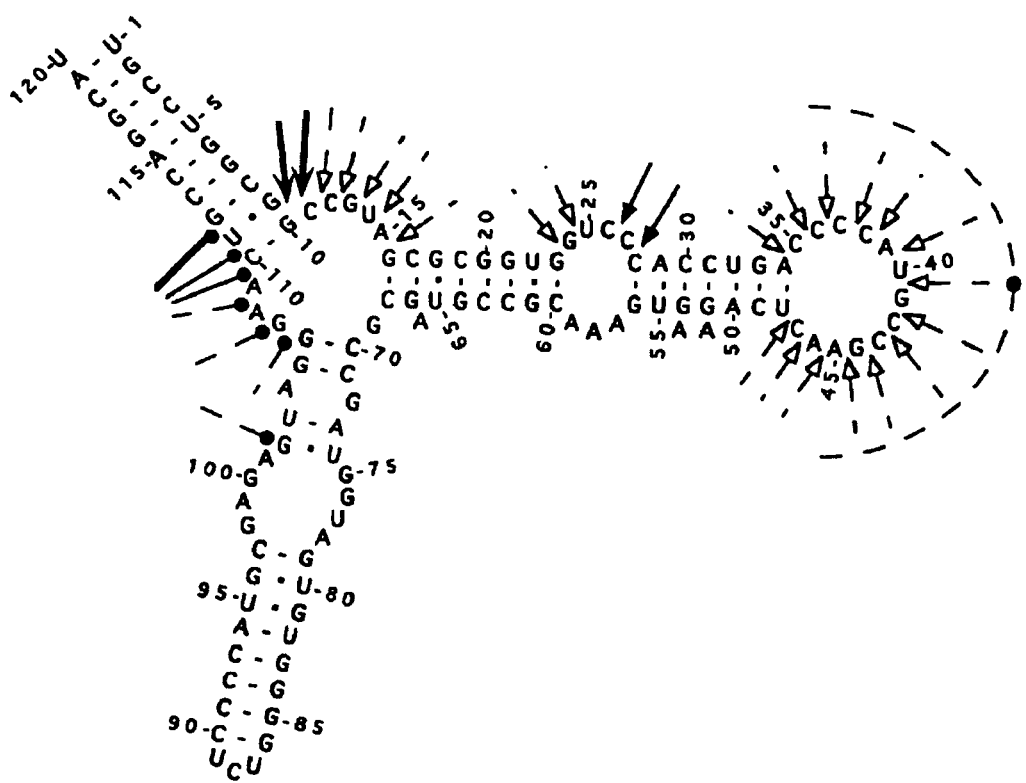
FIG. 16. A series of PNA constructs was synthesized to target one of the hairpin loops of commercially available *E. coil* 5S rRNA (SEQ ID NO:11) as the nucleic acid trigger. This rRNA has been thoroughly characterized by enzymatic and chemical probes, and is therefore a suitable initial model for studying and optimizing various catalytic drug releasing motifs in folded mRNA.
Figure 17:
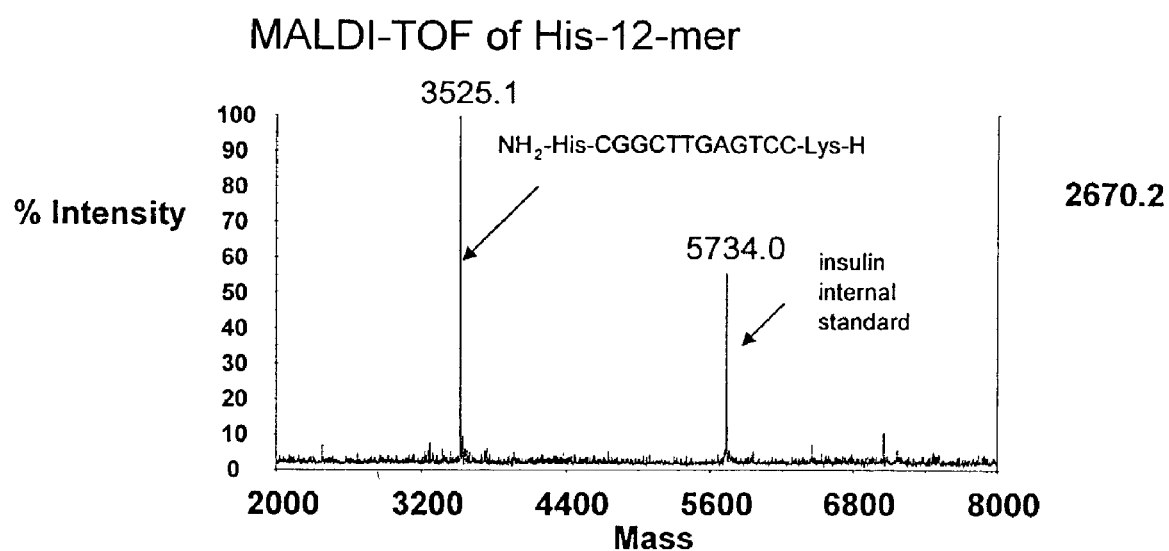
FIG. 17. A first PNA (SEQ ID NO:12) was synthesized on an ABI Expedite 8909 synthesizer located in my group, purified by reverse phase HPLC with 0.1% TFAICH3CN/H20 (in which the ester conjugates appear to be stable) and characterized by MALDI-TOF.
Figure 18:
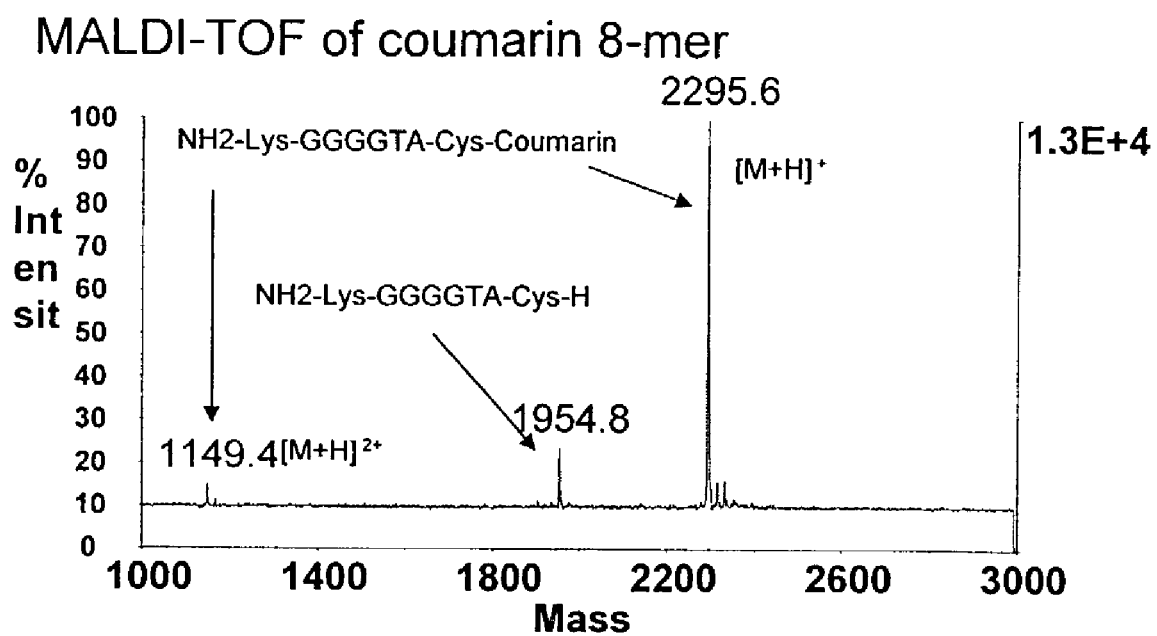
FIG. 18. A second PNA (SEQ ID NO:13:impurities as SEQ ID NO:14) was synthesized on an ABI Expedite 8909 synthesizer located in my group, purified by reverse phase HPLC with 0.1% TFA/CH$_3$CN/H$_{2O}$ (in which the ester conjugates appear to be stable) and characterized by MALDI-TOF.
Figure 19:
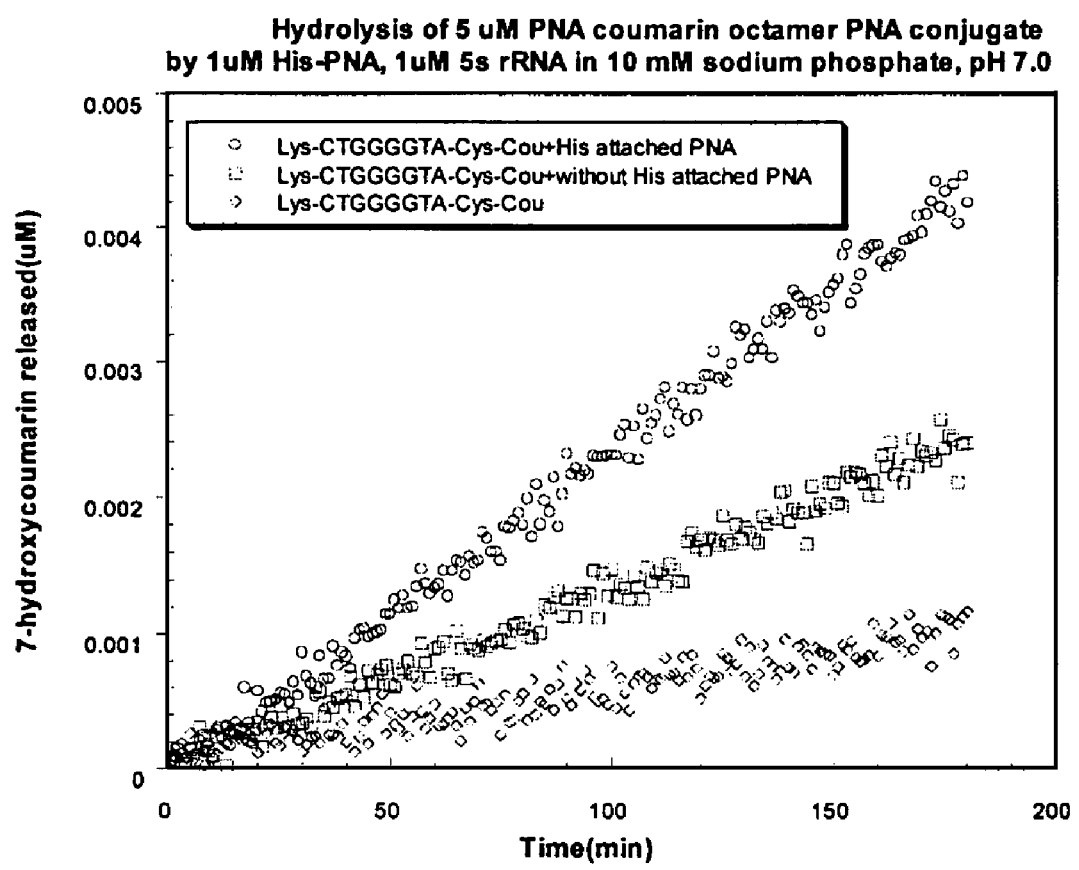
FIG. 19. In an unoptimized test of this system, it was found that hydroxycoumarin was released from the 8-mer PNA construct (SEQ ID NO:15) at a 2-fold higher rate in the presence of all three components, than in the presence of all three components minus the histidine (SEQ ID NO:16), and 4-fold faster than in the absence of the entire catalytic PNA (SEQ ID NO:17). In contrast, there was no difference in the rate of release of hydroxycoumarin from the 6-mer conjugate in the presence or absence of the histidine, or the catalytic component. (not shown).

Column 10, line 58, the figure reference "FIG. 9" should read --FIG. 15--.

Column 17, line 24, following the title of the section, a reference to --FIG. 3-- should be inserted.

Column 17, line 35, following the title of the section, a reference to --FIG. 3-- should be inserted.

Column 17, line 59, following the title of the section, a reference to --FIG. 3-- should be inserted.

Column 18, line 13, following the title of the section, a reference to --FIG. 4-- should be inserted.

UNITED STATES PATENT AND TRADEMARK OFFICE
CERTIFICATE OF CORRECTION

| | |
|---|---|
| PATENT NO. | : 7,445,891 B2 |
| APPLICATION NO. | : 10/201680 |
| DATED | : November 4, 2008 |
| INVENTOR(S) | : John-Stephen Taylor |

It is certified that error appears in the above-identified patent and that said Letters Patent is hereby corrected as shown below:

Column 19, line 7, following the title of the section, a reference to --FIG. 9-- should be inserted.

Column 19, line 33, following the title of the section, a reference to --FIG. 10-- should be inserted.

Column 19, line 48, following the title of the section, a reference to --FIG. 12-- should be inserted.

Column 19, line 61, following the title of the section, a reference to --FIG. 12-- should be inserted.

Column 20, line 15, following the title of the section, a reference to --FIG. 12-- should be inserted.

Column 20, line 38, following the title of the section, a reference to --FIG. 12-- should be inserted.

Column 20, line 61, following the title of the section, a reference to --FIG. 12-- should be inserted.

Column 21, line 20, following the title of the section, a reference to --FIG. 12-- should be inserted.

Column 21, line 44, following the title of the section, a reference to --FIG. 11, FIG. 13, FIG. 14-- should be inserted.

Column 22, line 20, following the title of the section, a reference to --FIG. 13, FIG. 14-- should be inserted.

UNITED STATES PATENT AND TRADEMARK OFFICE
CERTIFICATE OF CORRECTION

PATENT NO.        : 7,445,891 B2
APPLICATION NO.   : 10/201680
DATED             : November 4, 2008
INVENTOR(S)       : John-Stephen Taylor It is certified that error appears in the above-identified patent and that said Letters Patent is hereby corrected as shown below:

Column 22, line 40, following the title of the section, a reference to --FIG. 12, FIG. 15-- should be inserted.

Signed and Sealed this

Seventh Day of July, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,445,891 B2
APPLICATION NO.   : 10/201680
DATED             : November 4, 2008
INVENTOR(S)       : John-Stephen Taylor Page 1 of 1

It is certified that error appears in the above-identified patent and that said Letters Patent is hereby corrected as shown below:

In Column 7, line 27, the reference to "(SEQ ID NO: 18)" should read
--(SEQ ID NO:1)--.

Signed and Sealed this

Eleventh Day of August, 2009

David J. Kappos
*Director of the United States Patent and Trademark Office*

SEQUENCE LISTING

```
<160> NUMBER OF SEQ ID NOS: 19

<210> SEQ ID NO 1
<211> LENGTH: 8
<212> TYPE: DNA
<213> ORGANISM: Artificial
```

```
<220> FEATURE:
<223> OTHER INFORMATION: p-nitrophenol linked to an 8-mer
<220> FEATURE:
<223> OTHER INFORMATION: synthetic
<220> FEATURE:
<221> NAME/KEY: misc_feature
<222> LOCATION: (8)..(8)
<223> OTHER INFORMATION: p-nitrophenol

<400> SEQUENCE: 1 tcctgtca                                                                    8

<210> SEQ ID NO 2
<211> LENGTH: 15
<212> TYPE: DNA
<213> ORGANISM: Artificial
<220> FEATURE:
<223> OTHER INFORMATION: imidazole linked to a 15-mer
<220> FEATURE:
<223> OTHER INFORMATION: synthetic
<220> FEATURE:
<221> NAME/KEY: misc_feature
<222> LOCATION: (1)..(1)
<223> OTHER INFORMATION: imidazole

<400> SEQUENCE: 2
attacgctgg actct                                                           15

<210> SEQ ID NO 3
<211> LENGTH: 23
<212> TYPE: DNA
<213> ORGANISM: Artificial
<220> FEATURE:
<223> OTHER INFORMATION: Synthetic 23-mer

<400> SEQUENCE: 3
aggacagtta atgcgacctg aga                                                  23

<210> SEQ ID NO 4
<211> LENGTH: 24
<212> TYPE: DNA
<213> ORGANISM: Artificial
<220> FEATURE:
<223> OTHER INFORMATION: Synthetic hairpin structure

<400> SEQUENCE: 4
attacgcttg cgtaattgac agga                                                 24

<210> SEQ ID NO 5
<211> LENGTH: 15
<212> TYPE: DNA
<213> ORGANISM: Artificial
<220> FEATURE:
<223> OTHER INFORMATION: A synthetic 15-mer catalytic structure

<400> SEQUENCE: 5
attacgctgg actct                                                           15

<210> SEQ ID NO 6
<211> LENGTH: 23
<212> TYPE: DNA
<213> ORGANISM: Artificial
<220> FEATURE:
<223> OTHER INFORMATION: Synthetic 23-mer
<220> FEATURE:
<221> NAME/KEY: misc_feature
<222> LOCATION: (20)..(20)
<223> OTHER INFORMATION: n = A, C, G, or T
```

```
<400> SEQUENCE: 6
agagtccagc gtaattgacn gga                                            23

<210> SEQ ID NO 7
<211> LENGTH: 4
<212> TYPE: DNA
<213> ORGANISM: Artificial
<220> FEATURE:
<223> OTHER INFORMATION: Four-base oligodeoxynucleotide

<400> SEQUENCE: 7 gtca                                                                  4

<210> SEQ ID NO 8
<211> LENGTH: 6
<212> TYPE: DNA
<213> ORGANISM: Artificial
<220> FEATURE:
<223> OTHER INFORMATION: Six-base oligodeoxynucleotide

<400> SEQUENCE: 8 ctgtca                                                                6

<210> SEQ ID NO 9
<211> LENGTH: 8
<212> TYPE: DNA
<213> ORGANISM: Artificial
<220> FEATURE:
<223> OTHER INFORMATION: Eight-base oligodeoxynucleotide

<400> SEQUENCE: 9 tcctgtca                                                              8

<210> SEQ ID NO 10
<211> LENGTH: 8
<212> TYPE: DNA
<213> ORGANISM: Artificial
<220> FEATURE:
<223> OTHER INFORMATION: 8-mer prodrug
<220> FEATURE:
<223> OTHER INFORMATION: synthetic
<220> FEATURE:
<221> NAME/KEY: misc_feature
<222> LOCATION: (5)..(5)
<223> OTHER INFORMATION: n = A, C, G, or T

<400> SEQUENCE: 10 tcctntca                                                              8

<210> SEQ ID NO 11
<211> LENGTH: 117
<212> TYPE: RNA
<213> ORGANISM: E. coli

<400> SEQUENCE: 11
ugccuggcgg ccguagcgcg guggucccac cugaccccau gccgaacuca ggugaaacgc    60
cgugcgccga ugguagugug gggucucccc augcgagagu agggaacugc caggcau      117

<210> SEQ ID NO 12
<211> LENGTH: 12
<212> TYPE: DNA
<213> ORGANISM: Artificial
<220> FEATURE:
<223> OTHER INFORMATION: Peptide nucleic acid
<220> FEATURE:
<223> OTHER INFORMATION: synthetic
```

```
<220> FEATURE:
<221> NAME/KEY: misc_feature
<222> LOCATION: (1)..(1)
<223> OTHER INFORMATION: NH2-His
<220> FEATURE:
<221> NAME/KEY: misc_feature
<222> LOCATION: (12)..(12)
<223> OTHER INFORMATION: Lys-H

<400> SEQUENCE: 12
cggcttgagt cc                                                          12

<210> SEQ ID NO 13
<211> LENGTH: 6
<212> TYPE: DNA
<213> ORGANISM: Artificial
<220> FEATURE:
<223> OTHER INFORMATION: Peptide nucleic acid
<220> FEATURE:
<223> OTHER INFORMATION: synthetic
<220> FEATURE:
<221> NAME/KEY: misc_feature
<222> LOCATION: (1)..(1)
<223> OTHER INFORMATION: NH2-Lys
<220> FEATURE:
<221> NAME/KEY: misc_feature
<222> LOCATION: (6)..(6)
<223> OTHER INFORMATION: Cys-Coumarin

<400> SEQUENCE: 13 ggggta                                                                  6

<210> SEQ ID NO 14
<211> LENGTH: 6
<212> TYPE: DNA
<213> ORGANISM: Artificial
<220> FEATURE:
<223> OTHER INFORMATION: Peptide nucleic acid
<220> FEATURE:
<223> OTHER INFORMATION: synthetic
<220> FEATURE:
<221> NAME/KEY: misc_feature
<222> LOCATION: (1)..(1)
<223> OTHER INFORMATION: NH2-Lys
<220> FEATURE:
<221> NAME/KEY: misc_feature
<222> LOCATION: (6)..(6)
<223> OTHER INFORMATION: Cys-H

<400> SEQUENCE: 14 ggggta                                                                  6

<210> SEQ ID NO 15
<211> LENGTH: 8
<212> TYPE: DNA
<213> ORGANISM: Artificial
<220> FEATURE:
<223> OTHER INFORMATION: Peptide nucleic acid
<220> FEATURE:
<223> OTHER INFORMATION: synthetic
<220> FEATURE:
<221> NAME/KEY: misc_feature
<222> LOCATION: (1)..(1)
<223> OTHER INFORMATION: Lys
<220> FEATURE:
<221> NAME/KEY: misc_feature
<222> LOCATION: (8)..(8)
<223> OTHER INFORMATION: Cys-Coumarin-PNA-His
```

-continued

```
<400> SEQUENCE: 15 ctggggta                                                                 8

<210> SEQ ID NO 16
<211> LENGTH: 8
<212> TYPE: DNA
<213> ORGANISM: Artificial
<220> FEATURE:
<223> OTHER INFORMATION: Peptide nucleic acid
<220> FEATURE:
<223> OTHER INFORMATION: synthetic
<220> FEATURE:
<221> NAME/KEY: misc_feature
<222> LOCATION: (1)..(1)
<223> OTHER INFORMATION: Lys
<220> FEATURE:
<221> NAME/KEY: misc_feature
<222> LOCATION: (8)..(8)
<223> OTHER INFORMATION: Cys-Coumarin-PNA

<400> SEQUENCE: 16 ctggggta                                                                 8

<210> SEQ ID NO 17
<211> LENGTH: 8
<212> TYPE: DNA
<213> ORGANISM: Artificial
<220> FEATURE:
<223> OTHER INFORMATION: Peptide nucleic acid
<220> FEATURE:
<223> OTHER INFORMATION: synthetic
<220> FEATURE:
<221> NAME/KEY: misc_feature
<222> LOCATION: (1)..(1)
<223> OTHER INFORMATION: Lys
<220> FEATURE:
<221> NAME/KEY: misc_feature
<222> LOCATION: (8)..(8)
<223> OTHER INFORMATION: Cys-Coumarin

<400> SEQUENCE: 17 ctggggta                                                                 8

<210> SEQ ID NO 18
<211> LENGTH: 12
<212> TYPE: DNA
<213> ORGANISM: Artificial
<220> FEATURE:
<223> OTHER INFORMATION: Synthetic 12-mer

<400> SEQUENCE: 18
ggagcttgct cc                                                           12

<210> SEQ ID NO 19
<211> LENGTH: 8
<212> TYPE: DNA
<213> ORGANISM: Artificial
<220> FEATURE:
<223> OTHER INFORMATION: Synthetic 8-mer

<400> SEQUENCE: 19 tgacagga                                                                 8
```